US010383516B2

(12) United States Patent
Sakagawa

(10) Patent No.: US 10,383,516 B2
(45) Date of Patent: Aug. 20, 2019

(54) IMAGE GENERATION METHOD, IMAGE GENERATION APPARATUS, AND STORAGE MEDIUM

(71) Applicant: CANON KABUSHIKI KAISHA, Tokyo (JP)

(72) Inventor: Yukio Sakagawa, Tokyo (JP)

(73) Assignee: Canon Kabushiki Kaisha, Tokyo (JP)

(*) Notice: Subject to any disclaimer, the term of this patent is extended or adjusted under 35 U.S.C. 154(b) by 0 days.

(21) Appl. No.: 15/140,181

(22) Filed: Apr. 27, 2016

(65) Prior Publication Data

US 2016/0317018 A1 Nov. 3, 2016

(30) Foreign Application Priority Data

May 1, 2015 (JP) ................................. 2015-094339

(51) Int. Cl.
 *A61B 3/00* (2006.01)
 *A61B 3/12* (2006.01)
 *A61B 3/10* (2006.01)

(52) U.S. Cl.
 CPC .......... *A61B 3/1233* (2013.01); *A61B 3/0058* (2013.01); *A61B 3/102* (2013.01)

(58) Field of Classification Search
 CPC ..... A61B 3/0025; A61B 3/102; A61B 3/1233; A61B 3/0041
 USPC ................................................ 351/206, 246
 See application file for complete search history.

(56) References Cited

U.S. PATENT DOCUMENTS

| 2014/0160487 A1 | 6/2014 | Huang et al. |
| 2014/0221827 A1 | 8/2014 | Motaghiannezam et al. |
| 2015/0092195 A1 | 4/2015 | Blatter et al. |

FOREIGN PATENT DOCUMENTS

| CN | 104271031 A | 1/2015 |
| JP | 2003-052634 A | 2/2003 |
| JP | 2014-061085 A | 4/2014 |
| JP | 2015-511146 A | 4/2015 |
| WO | 2008/002839 A2 | 1/2008 |
| WO | 2012/170722 A2 | 12/2012 |

OTHER PUBLICATIONS

Fingler, J., et al., "Mobility and transverse flow visualization using phase variance contrast with spectral domain optical coherence tomography", Optics Express, Oct. 1, 2007, pp. 12636-12653, vol. 15, No. 20.

(Continued)

*Primary Examiner* — Jack Dinh
(74) *Attorney, Agent, or Firm* — Canon U.S.A., Inc., IP Division

(57) ABSTRACT

An image generation method includes an acquisition step of acquiring a plurality of pieces of tomogram data of a subject, the plurality of pieces of tomogram data representing cross-sections at a substantially identical position of the subject; a calculation step of calculating a motion contrast by using pieces of pixel data corresponding to one another among the plurality of pieces of tomogram data that have been acquired; a comparison step of comparing the motion contrast with a threshold; a generation step of generating a motion contrast image in which a brightness corresponding to the motion contrast that is lower than the threshold is lower than a brightness corresponding to the motion contrast that is higher than the threshold; and a change step of changing the threshold.

31 Claims, 13 Drawing Sheets

(56) References Cited

OTHER PUBLICATIONS

Mariampillai, A., et al., "Speckle variance detection of microvasculature using swept-source optical coherence tomography", Optics Letters, Jul. 1, 2008, pp. 1530-1532, vol. 33, No. 13.
Mariampillai, A., et al., "Optimized speckle variance OCT imaging of microvasculature", Optics Letters, Apr. 15, 2010, pp. 1257-1259, vol. 35, No. 8.

IMAGE GENERATION METHOD, IMAGE GENERATION APPARATUS, AND STORAGE MEDIUM

BACKGROUND

Field

The technique disclosed herein relates to an image generation method, an image generation apparatus, and a storage medium.

Description of the Related Art

Optical coherence tomography (OCT) has been put to practical use as a method for acquiring a tomogram of a measurement target such as a living body in a non-destructive and non-invasive manner. OCT is widely used particularly in the field of ophthalmology, for example, in an opthalmological diagnosis of a retina, in which a tomogram of the retina at an ocular fundus of a subject's eye is acquired.

In OCT, light reflected by a measurement target and light reflected by a reference mirror are caused to interfere with each other, an interference signal is detected, and time dependency or wavenumber dependency of the intensity of interfered light is analyzed to acquire a tomogram. An example of an optical coherence tomogram acquiring apparatus is a time domain OCT (TD-OCT) apparatus that acquires depth information about a measurement target by changing the position of a reference mirror. Another example is a spectral domain OCT (SD-OCT) apparatus that uses a broadband light source. Still another example is a swept source OCT (SS-OCT) apparatus that uses, as a light source, a wavelength-variable light source device capable of changing an oscillation wavelength. SD-OCT and SS-OCT are collectively referred to as Fourier domain OCT (FD-OCT).

In recent years, pseudo angiography using FD-OCT has been suggested, which is called OCT angiography (OCTA).

Fluoroangiography, which is angiography typically employed in modern clinical medicine, is performed by injecting a fluorescent dye (for example, fluorescein or indocyanine green) into a body or a part thereof. In fluoroangiography, blood vessels through which the fluorescent dye flows are two-dimensionally displayed. In contrast, OCT angiography enables pseudo angiography in a non-invasive manner and also enables three-dimensional display of a blood-flow network. Furthermore, OCT angiography produces a higher resolution result than fluoroangiography and is able to depict micro-vessels or blood flows at an ocular fundus.

As for OCT angiography, a plurality of methods have been suggested in accordance with a difference in a blood flow detection method. Fingler et al. "Mobility and transverse flow visualization using phase variance contrast with spectral domain optical coherence tomography", Optics Express, Vol. 15, No. 20, pp. 12637-12653 (2007) discloses a method for separating an OCT signal from a blood flow by extracting only a signal component in which time modulation occurs from the OCT signal. Optics Letters Vol. 33, Iss. 13, pp. 1530-1532 (2008) "Speckle variance detection of microvasculature using swept-source optical coherence tomography" discloses a method using variations in phase due to blood flows. Further, Mariampillai et. al., "Optimized speckle variance OCT imaging of microvasculature", Optics Letters 35, pp. 1257-1259 (2010) and United States Patent Application Publication No. 2014/221827 discloses a method using variations in intensity due to blood flows. In this specification, an image representing a signal component indicating time modulation in an OCT signal may be referred to as a motion contrast image, a pixel value of the motion contrast image may be referred to as a motion contrast value, and a data set of such motion contrast values may be referred to as motion contrast data.

In the above-described OCT angiography, however, it is difficult to easily acquire a motion contrast image suitable for diagnosis because, for example, a blood flow portion in the ocular fundus is not sufficiently clearly portrayed due to strong reflected light from a retinal pigment epithelium (RPE) or various noises.

SUMMARY

The technique disclosed herein approaches quick and appropriate drawing of a motion contrast image.

The technique disclosed herein has been made in view of the above-described issues and is directed to generating an appropriate motion contrast image.

The technique disclosed herein is also directed to obtaining the effects that are derived from the configurations according to the embodiments described below and that are not obtained from the related art.

An image generation method disclosed herein includes an acquisition step of acquiring a plurality of pieces of tomogram data of a subject, the plurality of pieces of tomogram data representing cross-sections at a substantially identical position of the subject; a calculation step of calculating a motion contrast by using pieces of pixel data corresponding to one another among the plurality of pieces of tomogram data that have been acquired; a comparison step of comparing the motion contrast with a threshold; a generation step of generating a motion contrast image in which a brightness corresponding to the motion contrast that is lower than the threshold is lower than a brightness corresponding to the motion contrast that is higher than the threshold; and a change step of changing the threshold.

Further features of the present invention will become apparent from the following description of exemplary embodiments with reference to the attached drawings.

DESCRIPTION OF THE EMBODIMENTS

Hereinafter, an image capturing apparatus according to an embodiment will be described with reference to the attached drawings. The configuration described in the following embodiment is an example, and the present invention is not limited to the embodiment. In the embodiment, a human eye (ocular fundus) is used as a subject, but the subject is not limited thereto and a skin of any part of the body may be used as a subject. Further, an ocular fundus is used as an image capturing target in the embodiment, but an anterior eye portion may be used as an image capturing target.

First Embodiment

In a first embodiment, a control unit 143 (described below) generates a tomogram from a three-dimensional optical coherent signal acquired through image capturing and calculates a motion contrast. Also, the control unit 143 adjusts a noise threshold by using structure information about a portion of the subject and acquires clarified information about three-dimensional blood flow in a portion of the subject.

Overall Configuration of Image Forming Apparatus

Figure 1:
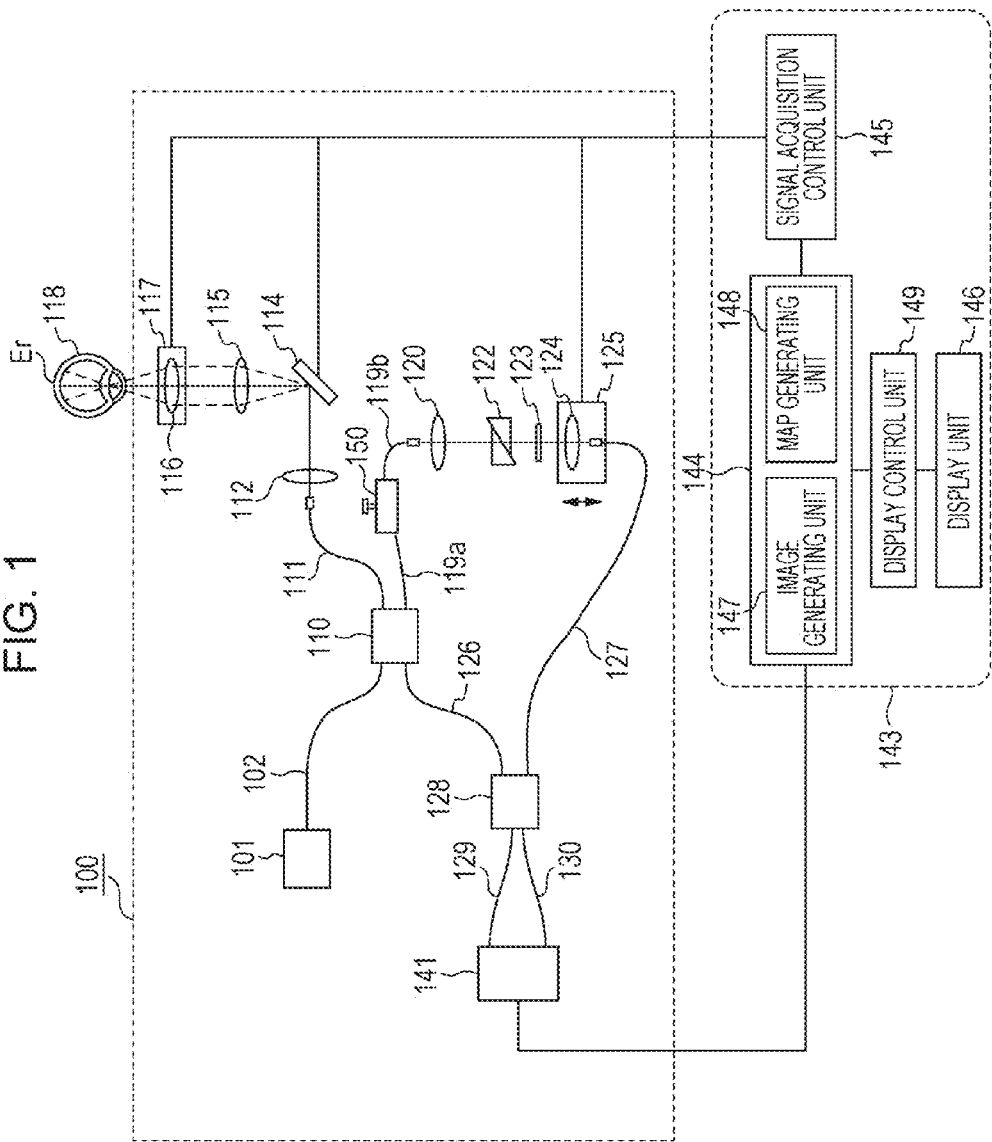
FIG. 1 is a diagram illustrating an overview of an example of the overall configuration of an apparatus according to a first embodiment.

FIG. 1 is a diagram illustrating an example configuration of an image forming apparatus using optical coherence tomography (OCT) according to this embodiment. The apparatus illustrated in FIG. 1 includes an OCT signal acquiring unit 100 that acquires an OCT signal and the control unit 143. The control unit 143 includes a signal processing unit 144, a signal acquisition control unit 145, a display unit 146, and a display control unit 149. The signal processing unit 144 includes an image generating unit 147 and a map generating unit 148. Here, the control unit 143 is a computer, for example. When a central processing unit (CPU) included in the computer executes a program stored in a storage device (not illustrated), the control unit 143 functions as the signal processing unit 144, the signal acquisition control unit 145, the image generating unit 147, the map generating unit 148, and the display control unit 149.

The control unit 143 may include a single CPU and a single storage device, or may include a plurality of CPUs and a plurality of storage devices. That is, one or more processing devices (CPUs) and one or more storage devices (a random access memory (RAM) and a read only memory (ROM)) are connected to one another. When the one or more processing devices execute a program stored in the one or more storage devices, the control unit 143 functions as the above-described units. The processing device is not limited to a CPU, and may be a field-programmable gate array (FPGA) or the like.

The configuration of the OCT signal acquiring unit 100 will be described. FIG. 1 is a diagram illustrating an example configuration of an OCT apparatus, which is an example of the OCT signal acquiring unit 100 according to this embodiment. The OCT apparatus is, for example, an SD-OCT apparatus or an SS-OCT apparatus. In this embodiment, it is assumed that the OCT apparatus is an SS-OCT apparatus.

Configuration of OCT Apparatus 100

The configuration of the OCT apparatus 100 will be described.

A light source 101 is a swept source (SS) type light source, and emits light while performing wavelength sweeping with a center sweep wavelength of 1050 nm and a sweep width of 100 nm. Such values of the wavelength and sweep width are examples, and the present invention is not limited by these values. Also, the values described below in the embodiments are examples, and the present invention is not limited by such values.

The light emitted from the light source 101 is led to a beam splitter 110 via an optical fiber 102 and is split into measurement light (also referred to as OCT measurement light) and reference light (also referred to as reference light corresponding to the OCT measurement light). The split ratio of the beam splitter 110 is 90 (reference light):10 (measurement light). The measurement light generated through split is emitted via an optical fiber 111 and is formed into parallel light by a collimator 112. The measurement light that has become parallel light enters a subject eye 118 via a galvano scanner 114 that performs scan at an ocular fundus Er of the subject eye 118 with measurement light, a scan lens 115, and a focus lens 116. Although the galvano scanner 114 is illustrated as a single mirror, it actually includes two galvano scanners (not illustrated) to raster scan the ocular fundus Er of the subject eye 118, that is, an X-axis scanner 114a and a Y-axis scanner 114b. The focus lens 116 is fixed onto a stage 117 and is capable of performing focus adjustment by being moved in an optical-axis direction. The galvano scanner 114 and the stage 117 are controlled by the signal acquisition control unit 145, and scanning can be performed with measurement light in a desired range of the ocular fundus Er of the subject eye 118 (also referred to as a tomogram acquisition range, a tomogram acquisition position, or a measurement light irradiation position).

Although a detailed description is not given in this embodiment, a tracking function may be provided in which a movement of the ocular fundus Er is detected and the mirror of the galvano scanner 114 is caused to track the movement of the ocular fundus Er to perform scanning. Tracking may be performed by using a typical technique, and may be performed in real time or in post-processing. For example, there is a method of using a scanning laser ophthalmoscope (SLO). In this method, a two-dimensional image in a plane vertical to an optical axis of the ocular fundus Er (ocular fundus surface image) is chronologically acquired by using an SLO, and a characteristic portion such as a branch of a blood vessel is extracted from the image. A movement at the characteristic portion in the acquired two-dimensional image is calculated as an amount of movement of the ocular fundus Er, the calculated amount of movement is fed back to the galvano scanner 114, and thereby real-time tracking can be performed.

The measurement light is caused to enter the subject eye 118 by the focus lens 116 on the stage 117 and is focused on the ocular fundus Er. The measurement light with which the ocular fundus Er has been irradiated is reflected or scattered at each retinal layer and returns along the above-described optical path to the beam splitter 110. The returned measurement light that has entered the beam splitter 110 enters a beam splitter 128 via an optical fiber 126.

On the other hand, the reference light generated through split at the beam splitter 110 is emitted via an optical fiber 119a, a polarization controller 150, and an optical fiber 119b, and is formed into parallel light by a collimator 120. The polarization controller 150 is capable of changing the polarization state of the reference light to a desired polarization state. The reference light enters an optical fiber 127 via a dispersion compensation glass 122, an ND filter 123, and a collimator 124. One end of the collimator 124 and one end of the optical fiber 127 are fixed on a coherence gate stage 125, which is controlled by the signal acquisition control unit 145 so as to be driven in the optical-axis direction in accordance with a difference in ocular axis length of a subject. In this embodiment, the optical path length of the reference light is changed, but it is sufficient that a difference in optical path length between the optical path of the measurement light and the optical path of the reference light can be changed.

The reference light that has passed through the optical fiber 127 enters the beam splitter 128. At the beam splitter 128, the returned measurement light and the reference light are combined into coherent light, which is then divided into two coherent light beams. The two coherent light beams generated through division have phases inverted to each other (hereinafter referred to as a positive component and a negative component). The positive component of the coherent light beam enters one input port of a detector 141 via an optical fiber 129. On the other hand, the negative component of the coherent light beam enters the other input port of the detector 141 via an optical fiber 130. The detector 141 is a differential detector. When two coherent light beams having phases inverted by 180 degrees to each other are input to the detector 141, the detector 141 removes a direct current component and outputs a coherent signal containing only a coherent component.

The coherent light detected by the detector 141 is output as an electric signal (coherent signal) corresponding to the intensity of the light and is input to the signal processing unit 144, which is an example of a tomogram generating unit.

Control Unit 143

The control unit 143 for controlling the overall apparatus will be described.

The control unit 143 includes the signal processing unit 144, the signal acquisition control unit 145, the display unit 146, and the display control unit 149. The signal processing unit 144 includes the image generating unit 147 and the map generating unit 148. The image generating unit 147 has a function of generating a brightness image and a motion contrast image from an electric signal (coherent signal) transmitted from the detector 141. The map generating unit 148 has a function of generating layer information (retina segmentation) from the brightness image.

The signal acquisition control unit 145 controls the individual units in the manner described above. The signal processing unit 144 generates an image, analyzes the generated image, and generates visible information representing the analysis result on the basis of a coherent signal output from the detector 141.

The image and analysis result generated by the signal processing unit 144 are transmitted to the display control unit 149. The display control unit 149 displays the image and analysis result on a display screen of the display unit 146. Here, the display unit 146 is a liquid crystal display or the like. The image data generated by the signal processing unit 144 may be transmitted to the display unit 146 in a wired or wireless manner after being transmitted to the display control unit 149. In this embodiment, the display unit 146 is included in the control unit 143, but the present invention is not limited thereto. The display unit 146 may be provided separately from the control unit 143, and may be, for example, a tablet, which is an example of a device portable by a user. In this case, a touch panel function may be installed in the display unit 146 so that a display position of an image can be changed, an image can be enlarged or reduced, or an image to be displayed can be changed on the touch panel.

The process of acquiring information regarding a cross-section at one point of the subject eye 118 has been described above. Such a process of acquiring information regarding a cross-section in the depth direction of the subject eye 118 is referred to as A-scan. Scan for acquiring information regarding a cross-section of the subject eye 118 in the direction orthogonal to the direction of A-scan, that is, a two-dimensional image, is referred to as B-scan. Scan in the direction orthogonal to a tomogram acquired through B-scan is referred to as C-scan. More specifically, in the case of performing two-dimensional raster scan in the plane of an ocular fundus in order to acquire a three-dimensional tomogram, high-speed scan is referred to as B-scan, whereas low-speed B-scan in the direction orthogonal to the direction of B-scan is referred to as C-scan. A-scan and B-scan allow a two-dimensional tomogram to be acquired. A-scan, B-scan, and C-scan allow a three-dimensional tomogram to be acquired. B-scan and C-scan are performed by the above-described galvano scanner 114.

The X-axis scanner 114a and the Y-axis scanner 114b (not illustrated) are formed of deflection mirrors located such that their rotation axes are orthogonal to each other. The X-axis scanner 114a performs scan in the X-axis direction and the Y-axis scanner 114b performs scan in the Y-axis direction. The X-axis direction and the Y-axis direction are perpendicular to the eye-axis direction of an eyeball and are perpendicular to each other. The line scan direction such as the directions of B-scan and C-scan do not necessarily match the X-axis direction and the Y-axis direction. Thus, the line scan direction of B-scan and C-scan can be appropriately determined in accordance with a two-dimensional or three-dimensional tomogram to be captured.

Scan Pattern

Next, an example of a scan pattern according to this embodiment will be described with reference to FIG. 2.

OCT angiography measures chronological changes in an OCT coherent signal, caused by blood flows, and thus requires a plurality of measurements at the same place (or substantially the same place). In this embodiment, the OCT apparatus repeats B-scan at the same place m times and performs scan to move to y positions at n locations.

Figure 2:
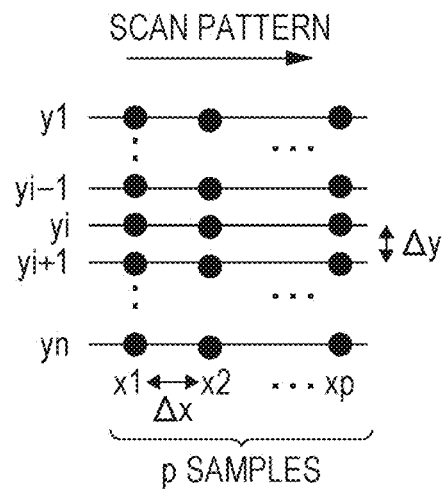
FIG. 2 is a diagram illustrating an example of a scan pattern according to the first embodiment.

A specific scan pattern is illustrated in FIG. 2. B-scan is repeatedly performed m times for the y positions at the n locations (y1 to yn) on an ocular fundus plane.

As m increases, the number of times of measurement at the same place increases, and accordingly the accuracy of detecting blood flows enhances. On the other hand, scan time increases, which may cause motion artifacts in an image due to eye movements (involuntary eye movements during fixation) during scan and an increased burden of a subject. In this embodiment, m is set to 4 in consideration of the balance between both. The control unit 143 may change m in accordance with the speed of A-scan performed by the OCT apparatus and motion analysis of an ocular fundus surface image of the subject eye 118.

In FIG. 2, p represents the number of samples of A-scan in each B-scan. That is, the size of a plane image is determined by p×n. If p×n is large, scan can be performed over a wide range with the same measurement pitch, but scan time increases to result in the above-described motion artifacts and burden on a patient. In this embodiment, scan is performed with n=p=300 in consideration of the balance between both. Note that the values n and p can be freely changed.

In FIG. 2, Δx represents an interval between adjoining x positions (x pitch), and Δy represents an interval between adjoining y positions (y pitch). In this embodiment, the x pitch and y pitch are determined to be one half of the beam spot diameter of light with which an ocular fundus is irradiated. In one embodiment, the x pitch and y pitch is 10 μm. With the x pitch and y pitch being one half of the beam spot diameter on the ocular fundus, a high-definition image can be generated. Decreasing the x pitch and y pitch to be smaller than one half of the beam spot diameter on the ocular fundus has a small effect of enhancing the definition of the image to be generated.

If the x pitch and y pitch are increased to be larger than one half of the beam spot diameter on the ocular fundus, the definition degrades, but an image in a wide range can be acquired with small data capacity. The x pitch and y pitch may be freely changed in accordance with clinical requirements.

The scan range according to this embodiment is p×Δx=3 mm in the x direction and n×Δy=3 mm in the y direction.

Figure 3:
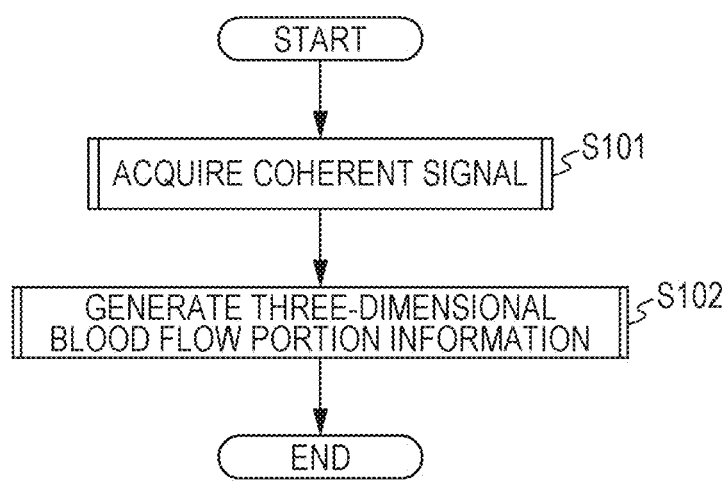
FIG. 3 is a diagram illustrating an example of an overall processing procedure according to the first embodiment.

Next, a procedure of a specific process of an image formation method according to this embodiment will be described with reference to FIG. 3.

In step S101, the signal acquisition control unit 145 controls the OCT signal acquiring unit 100 to acquire an OCT signal (also referred to as a coherent signal). The details of this step will be described below. In step S102, the control unit 143 generates display information (also referred to as information of three-dimensional blood flow in a portion of a subject). The details of this step will be described below. After these steps have been performed, the procedure of the process of the image formation method according to this embodiment is finished.

Coherent Signal Acquisition Procedure

Figure 4:
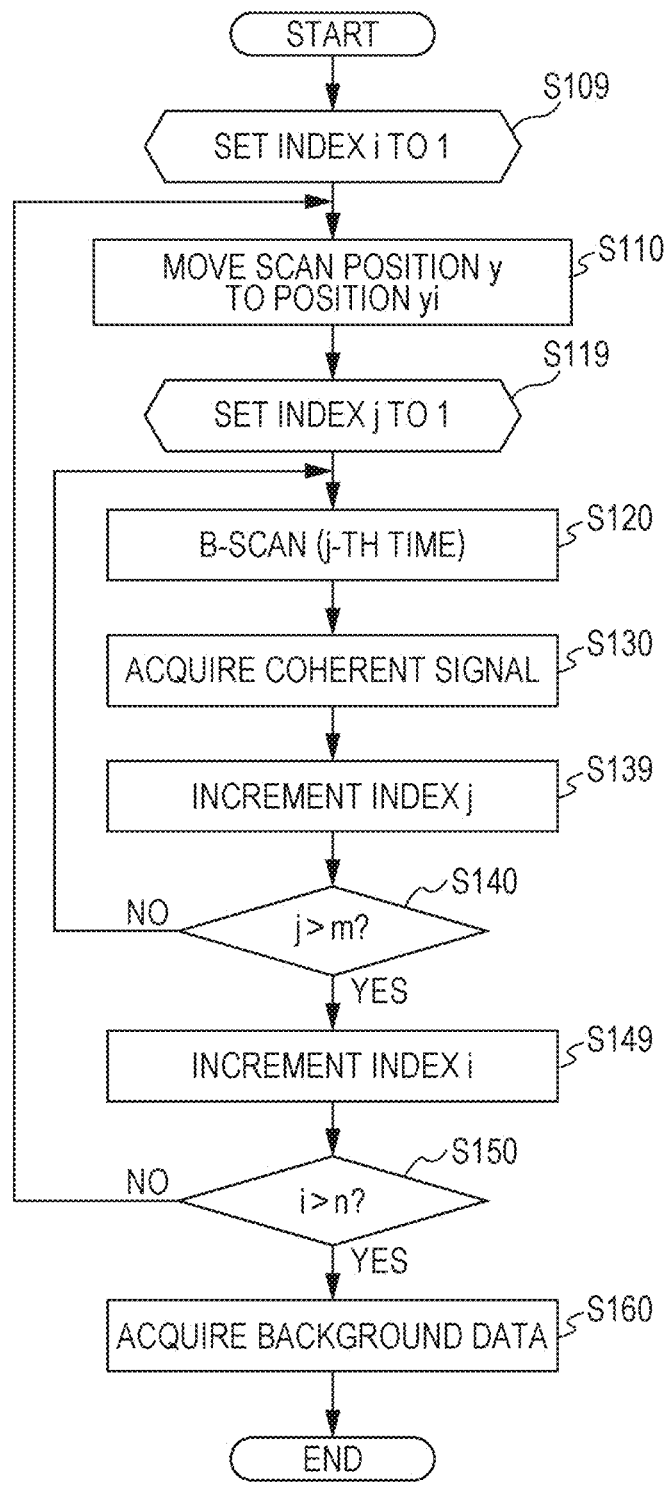
FIG. 4 is a diagram illustrating an example of an interference signal acquisition procedure according to the first embodiment.

Next, a procedure of a specific process of acquiring a coherent signal in step S101 according to this embodiment will be described with reference to FIG. 4. In step S109, the signal acquisition control unit 145 sets an index i of a position y1 in FIG. 2 to 1. In step S110, the OCT apparatus moves the scan position to the position yi. In step S119, the signal acquisition control unit 145 sets an index j of repeated B-scan to 1. In step S120, the OCT apparatus performs B-scan.

In step S130, the detector 141 detects a coherent signal for each A-scan, and the coherent signal is stored in the signal processing unit 144 via an A/D converter (not illustrated). The signal processing unit 144 acquires p samples of the coherent signals acquired through A-scan and regards them as a coherent signal of one B-scan.

In step S139, the signal acquisition control unit 145 increments the index j of repeated B-scan.

In step S140, the signal acquisition control unit 145 determines whether or not the index j is larger than a certain number of times (m times). That is, the signal acquisition control unit 145 determines whether or not B-scan at the position yi has been repeated m times. If B-scan has not been repeated m times, the process returns to step S120, and B-scan measurement at the same position is repeated. If B-scan has been repeated m times, the process proceeds to step S149. In step S149, the signal acquisition control unit 145 increments the index i of the position yi. In step S150, the signal acquisition control unit 145 determines whether or not the index i is larger than the number of times of measurement (n) at a certain Y position, that is, whether or not B-scan has been performed at all the y positions at the n locations. If the index i is equal to or smaller than the number n at the certain Y position (NO in step S150), the process returns to step S110, and measurement at the next measurement position is repeated. If measurement at the certain Y position has been performed n times (YES in step S150), the process proceeds to step S160.

In step S160, the OCT apparatus acquires background data. The OCT apparatus performs A-scan 100 times in a state where a shutter 85 is closed. The signal acquisition control unit 145 averages the 100 A-scans and stores the average. The number of times of measurement in the background is not limited to 100.

After the above-described steps have been performed, the coherent signal acquisition procedure according to this embodiment ends.

Signal Processing Procedure

Next, the details of the process of generating information about a three-dimensional blood flow in a portion of a subject (generating three-dimensional blood flow portion information), in step S102 according to this embodiment will be described with reference to FIG. 5.

In this embodiment, it is necessary to calculate a motion contrast of OCT angiography in order to generate three-dimensional blood flow portion information from OCT angiography information.

Here, a motion contract is defined as the contrast between a tissue with flows (for example, blood) and a tissue without flows among tissues of a subject. A feature value representing a motion contrast is simply defined as a motion contrast (or a motion contrast feature value or a motion contrast value). The motion contrast will be described below with reference to FIG. 5.

Figure 5:
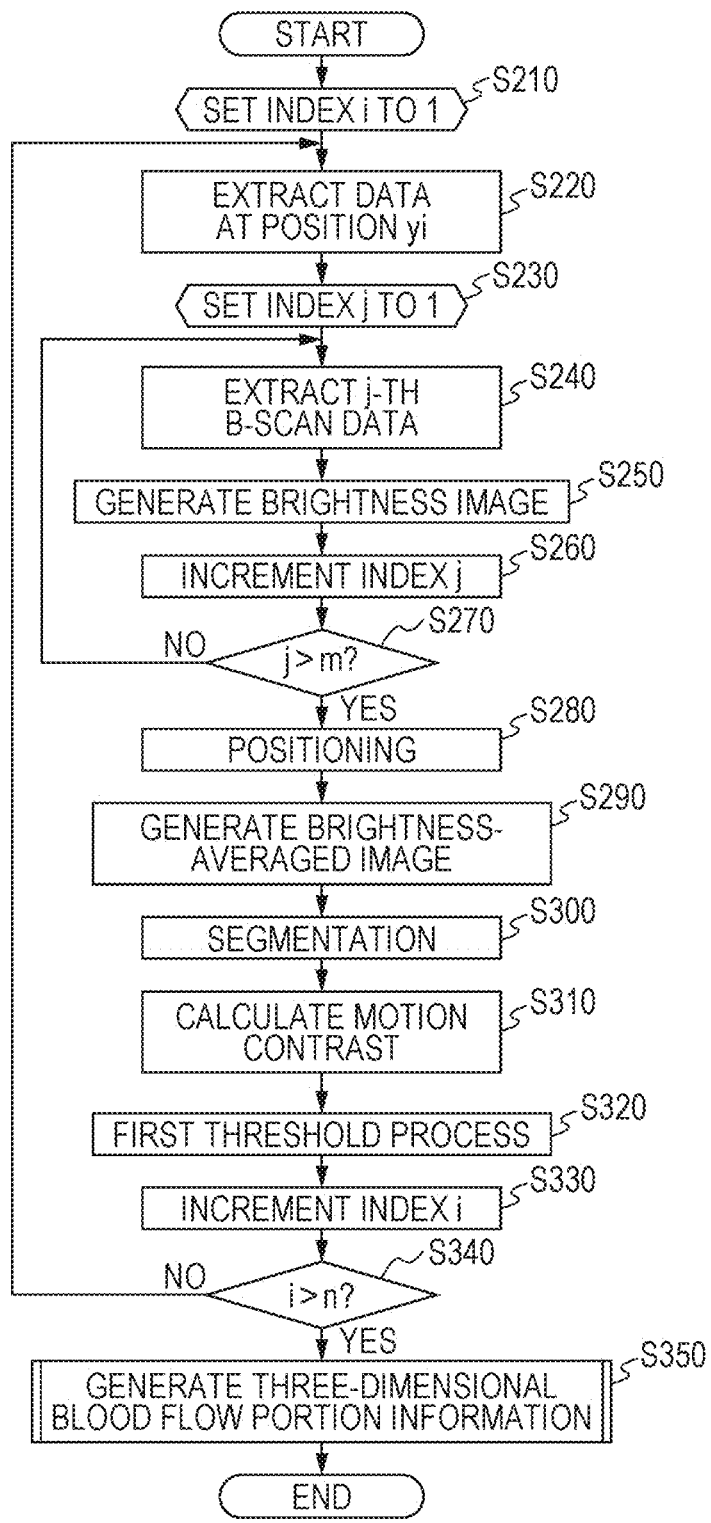
FIG. 5 is a diagram illustrating an example of a signal processing procedure according to the first embodiment.

In step S210 of FIG. 5, the signal processing unit 144 sets the index i of the position yi to 1. In step S220, the signal processing unit 144 extracts coherent signals of repeated B-scan (m times) at the position yi. In step S230, the signal processing unit 144 sets the index j of repeated B-scan to 1. In step S240, the signal processing unit 144 extracts the j-th B-scan data.

In step S250, the signal processing unit 144 performs a typical reconstruction process on the coherent signal of the B-scan data acquired in step S240 and thereby generates a brightness image of a tomogram.

First, the image generating unit 147 removes fixed pattern noise composed of background data from the coherent signal. The removal of fixed pattern noise is performed by extracting fixed pattern noise by averaging A-scan signals of a plurality of pieces of background data that have been detected and subtracting the fixed pattern noise from the input coherent signal. Subsequently, the image generating unit 147 performs a desired window function process to optimize depth resolution and dynamic range that have a tradeoff relationship in a case where Fourier transform is performed in a limited section. Subsequently, the image generating unit 147 performs an FFT process to generate a brightness image of a tomogram. In step S260, the signal processing unit 144 increments the index j of repeated B-scan. In step S270, the signal processing unit 144 determines whether or not the index j is larger than m, that is, whether or not brightness calculation for B-scan at the position yi has been repeated m times. If a negative determination is made, the process returns to step S240, and brightness calculation of repeated B-scan at the same Y position is repeated. That is, the image generating unit 147 acquires a plurality of pieces of tomogram data (tomograms) of a subject representing cross-sections at a substantially identical position of the subject. "Substantially identical position" includes an actual identical position and almost identical position. Ideally scanning is performed plural times at an actual identical position. But in reality, scanning may be performed plural times at almost identical position because of involuntary eye movement. If a tracking technique is used for tracking the eye movement, scanning may be performed plural times at almost identical position because of imperfectness of the tracking technique.

On the other hand, if a positive determination is made in step S270, the process proceeds to step S280. In step S280, the signal processing unit 144 performs positioning of m frames of repeated B-scan at a certain yi position. Specifically, the signal processing unit 144 selects one of the m frames as a template. The frame to be used as a template may be selected by calculating correlations among all the combinations of the frames, calculating the sums of correlation coefficients for the individual frames, and selecting the frame corresponding to a maximum sum. Subsequently, the signal processing unit 144 compares the template with each frame and acquires the amount of positional deviation ($\delta X$, $\delta Y$, $\delta \theta$). Specifically, the signal processing unit 144 calculates normalized cross-correlation (NCC), which is an index indicating similarity, by changing the position and angle of the template image, and acquires a difference in image position when the NCC value is maximum as an amount of positional deviation.

In an embodiment of the present invention, the index indicating similarity may be changed as long as the index indicates similarity in image feature between the template and each frame. For example, sum of absolute difference (SAD), sum of squared difference (SSD), or zero-means normalized cross-correlation (ZNCC) may be used. Alternatively, phase only correlation (POC) or rotation invariant phase only correlation (RIPOC) may be used.

Subsequently, the signal processing unit 144 applies position correction to the m−1 frames other than the template in accordance with the amount of positional deviation ($\delta X$, $\delta Y$, $\delta \theta$), and performs positioning on the m frames.

In step S290, the signal processing unit 144 averages the brightness images subjected to positioning in step S280 and thereby generates a brightness-averaged image.

In step S300, the map generating unit 148 performs retina segmentation (acquires portion information) by using the brightness-averaged image generated by the signal processing unit 144 in step S290. In the first embodiment, this step is skipped. The description of this step will be given in a second embodiment.

In step S310, the image generating unit 147 calculates a motion contrast. In this embodiment, the image generating unit 147 calculates a dispersion value of signal intensity (brightness) for the pixels at the same position in the brightness images of tomograms of m frames output from the signal processing unit 144 in step S300, and the dispersion value is regarded as a motion contrast. That is, the image generating unit 147 calculates a motion contrast by using pieces of pixel data corresponding to one another among a plurality of pieces of tomogram data that have been acquired. Instead of the dispersion value, any of a standard deviation, a difference value, a non-correlation value, and a correlation value may be used. A phase may be used instead of the signal intensity.

There are various ways of calculating a motion contrast. In an embodiment of the present invention, any index indicating a change in brightness value of each pixel of a plurality of B-scan images at the same Y position may be used as a feature value of a motion contrast. Alternatively, as a motion contrast, a variation coefficient normalized with an average value of the same pixels in individual frames may be used instead of a dispersion value of the pixels at the same position of brightness images of tomograms of m frames. In this case, a motion contrast is independent of pixel values indicating the structure of a retina, and a more sensitive motion contrast can be acquired. However, in a motion contrast, a noise component in a small pixel value is relatively emphasized due to various factors, such as positioning errors and camera noise. Thus, in a layer that does not include many capillaries, for example, it is difficult to separate noise from a blood flow region. Thus, the image processing method according to the embodiment of the present invention operates more effectively.

In step S320, the signal processing unit 144 performs a first threshold process on the motion contrast calculated by the image generating unit 147. The value of a first threshold is set to be an average brightness of noise floor+2$\sigma$ by extracting an area in which only random noise is displayed in noise floor from the brightness-averaged image output from the signal processing unit 144 in step S290 and calculating a standard deviation $\sigma$. The signal processing unit 144 sets the value of a motion contrast corresponding to the region where the brightness is equal to or smaller than the threshold to 0.

With the first threshold process in step S320, in which motion contrast derived from a change in brightness caused by random noise is removed, noise can be reduced.

As the value of the first threshold decreases, the detection sensitivity for motion contrast increases and a noise component increases. As the value of the first threshold increases, noise reduces and the detection sensitivity for motion contrast decreases.

In this embodiment, the threshold is set to be an average brightness of noise floor+2$\sigma$, but the threshold is not limited thereto.

In step S330, the signal processing unit 144 increments the index i of the position yi.

In step S340, the signal processing unit 144 determines whether or not the index i is larger than n, that is, whether or not positioning, calculation of a brightness-averaged image, calculation of a motion contrast, and a threshold process have been performed at all the y positions at the n locations. If a negative determination is made, the process returns to step S220. If a positive determination is made, the process proceeds to step S350.

The completion of step S340 means that a brightness-averaged image of each pixel of B-scan images at all the Y positions (Z depth vs X-direction data) and three-dimensional data of a motion contrast have been acquired. The B-scan images at a plurality of Y positions correspond to three-dimensional tomogram data.

Figure 6:
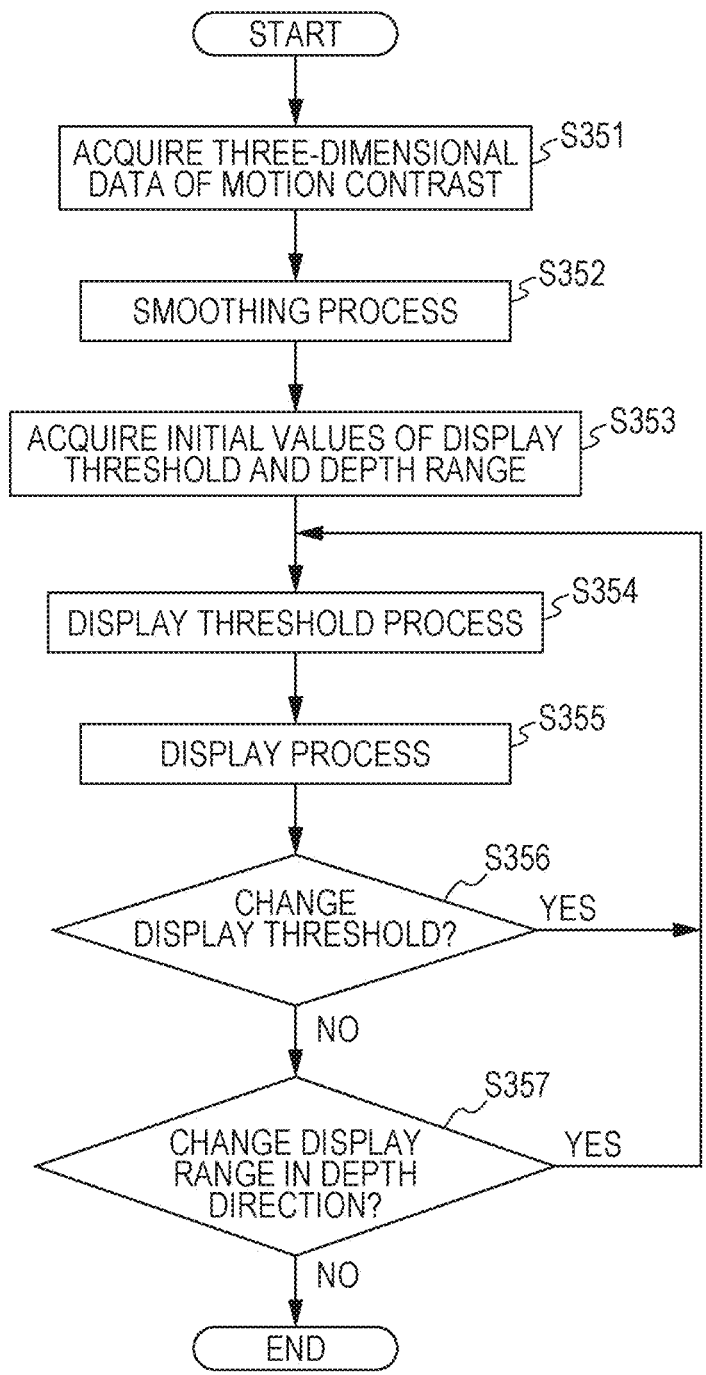
FIG. 6 is a diagram illustrating an example of a three-dimensional blood flow portion information acquisition procedure according to the first embodiment.

In step S350, the signal processing unit 144 performs a process of generating three-dimensional blood flow portion information by using the three-dimensional data of a motion contrast. FIG. 6 illustrates the details of step S350.

In step S351, the signal processing unit 144 acquires the three-dimensional data of a motion contrast, which has already been acquired.

In step S352, the signal processing unit 144 performs a smoothing process on the three-dimensional data of a motion contrast to remove noise while keeping blood flow portion information.

The following methods are available although the optimum smoothing process varies according to the nature of a motion contrast.

There are a smoothing method of outputting a maximum value of a motion contrast from nx×ny×nz voxels near a target pixel; a smoothing method of outputting an average value of a motion contrast of nx×ny×nz voxels near a target pixel; a smoothing method of outputting a median value of a motion contrast of nx×ny×nz voxels near a target pixel; a smoothing method of assigning a weight based on a distance to a motion contrast of nx×ny×nz voxels near a target pixel; a smoothing method of assigning a weight to a motion contrast of nx×ny×nz voxels near a target pixel in accordance with a difference between a weight based on a distance and a pixel value of a target pixel; and a smoothing method of outputting a value using a weight corresponding to the similarity between a motion contrast pattern in a small region around a target pixel and a motion contrast pattern in a small region around surrounding pixels.

Alternatively, a method for performing smoothing while keeping other blood flow portion information may be used.

In step S353, the signal processing unit 144 acquires, from the display control unit 149, an initial value of a threshold for determining pixels to be displayed and an initial value of a range in the depth direction to be displayed. The initial value of the display range is usually about a quarter in the depth direction and corresponds to a position almost including the range of a surface layer of a retina. The initial value of the display range does not correspond to the entire range in the depth direction because a main vascular plexus and a capillary plexus in a surface layer portion are to be displayed so that they are easily seen. If the surface layer portion including a main vascular plexus and a capillary plexus and an RPE layer with a lot of noise that do not include blood vessels are displayed at the same time, it is difficult to identify the main vascular plexus and capillary plexus in the surface layer portion. The method for determining the initial value of the display threshold will be described below.

Figure 7A:
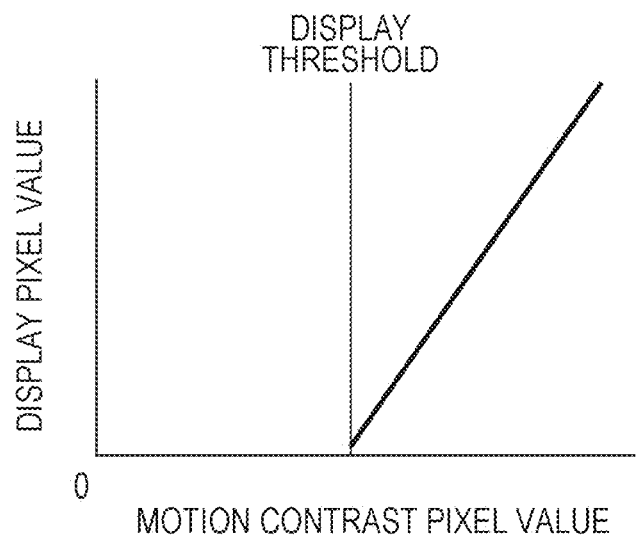
FIGS. 7A and 7B are diagrams illustrating an example of a method for converting a motion contrast pixel value to a display pixel value according to the first embodiment.
Figure 7B:
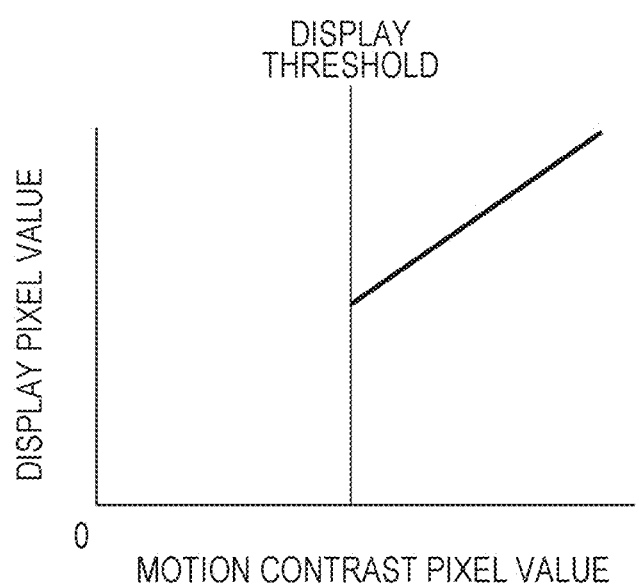

In step S354, a display threshold process of displaying pixels exceeding the initial value of the display threshold is performed on the three-dimensional data that has been subjected to a smoothing process by using the initial value. An example of converting a motion contrast pixel value to a display pixel value in this process is illustrated in FIGS. 7A and 7B. FIG. 7A illustrates an example in which a pixel value equal to or smaller than the display threshold is zero, and display pixel values proportional to a pixel value on the threshold to a pixel value of the maximum intensity are assigned. FIG. 7B illustrates an example in which display values acquired by multiplying a pixel value equal to or smaller than the display threshold by 0 and multiplying a pixel value equal to or larger than the display threshold by 1 are assigned. That is, a pixel value (brightness) corresponding to a motion contrast lower than the threshold is smaller than a pixel value (brightness) corresponding to a motion contrast higher than the threshold. In any case, a motion contrast equal to or lower than the display threshold is invalidated, and display is performed such that a region with a motion contrast having a connection to be displayed is separated. That is, the value of a motion contrast is controlled in accordance with a result of comparison between the motion contrast and the threshold. The process in step S354 corresponds to an example of a comparison step of comparing a motion contrast with the threshold and an invalidation step of invalidating a motion contrast equal to or lower than the threshold on the basis of the result of comparison.

In step S355, the display control unit 149 causes the display unit 146 to display the motion contrast image that has been subjected to the display threshold process illustrated in FIGS. 7A and 7B. Specifically, a motion contrast image in which a brightness corresponding to a motion contrast that is lower than the threshold is lower than a brightness corresponding to a motion contrast that is higher than the threshold is displayed on the display unit 146. That is, the process in step S355 corresponds to an example of a generation step of generating a motion contrast image on the basis of a motion contrast after the invalidation process has been performed. For example, the display step S355 is designed to display the GUI and three-dimensional motion contrast image illustrated in FIG. 8B and display them on the display unit 146. Reference numeral 400 denotes a parallelogram region prepared in the display unit 146 and is a display region frame for projecting and displaying a calculated three-dimensional motion contrast image. Beside the frame, a slider 407 for adjusting the range in the depth direction of the three-dimensional motion contrast image to be displayed is displayed. A tester drags, with a mouse, for example, an operation portion end 401 or 402 of the slider 407, and is thereby able to designate the range in the depth direction of the three-dimensional motion contrast image to be displayed on the display unit 146. Also, the tester (operator) is able to change a depth position of display without changing the width of the depth range for display, by dragging a center portion of the operation unit of the slider 407. In FIG. 8A, a tomogram of a three-dimensional motion contrast image is illustrated for describing the corresponding depth. Bright lines 403 and 404 on the tomogram are positions on the tomogram corresponding to the operation portion ends 401 and 402. In the display step, only the motion contrast image in a region 405 sandwiched between the bright lines 403 and 404 is displayed in the display region frame 400. For example, the display control unit 149 may cause the display unit 146 to display all the images illustrated in FIGS. 8A and 8B or display only the image illustrated in FIG. 8B.

Further, another slider 406 for adjusting a threshold for determining the pixel to be displayed is provided below the display region frame 400. When the tester drags the slider 406 with a mouse, for example, the display threshold is changed in step S356 in FIG. 6, the process returns to step S354, and the three-dimensional motion contrast image to be displayed is updated. The process in step S356 corresponds to an example of a change step of changing the threshold. The repeated execution of steps S354 and S355 corresponds to repeated execution of a generation step of generating a motion contrast image in accordance with a change in the threshold and a display step of displaying the motion contrast image.

In this case, if a setting is made so that the threshold can be changed with a relative value with respect to the initial value, an equivalent effect can be acquired for different pieces of data of different targets such as subject eyes or portions. With the above-described configuration, a tester is able to voluntarily change the depth range for display and is also able to set an optimum display threshold for the selected depth range. When the tester drags, with a mouse, the operation portion end 401 or 402 to change the display range in the depth direction, the display range is changed in step S357. The process then returns to step S354 and the three-dimensional motion contrast image to be displayed is updated. That is, the motion contrast image to be displayed is updated in accordance with a change in the display range. Here, the process in step S357 corresponds to an example of a set step of setting the display range in the depth direction of a motion contrast image. The execution of step S355 after the execution of step S357 corresponds to an example of a display step of displaying a motion contrast image on the basis of the display range that has been set.

In the description given above, the tomogram illustrated in FIG. 8A is used only for the description. If this tomogram is simultaneously displayed in the display step, the tester is able to easily set the depth range for display. The tomogram may be provided beside the display region frame 400 so as to clearly indicate the depth direction. The position corresponding to the tomogram to be displayed may be displayed such that the position is superposed on a three-dimensional motion contrast image. For example, the display control unit 149 may superpose a line corresponding to the tomogram on the three-dimensional motion contrast image.

Figure 9A:
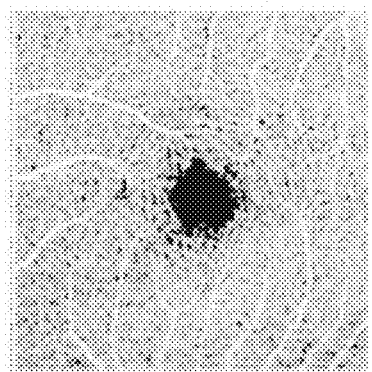
FIGS. 9A to 9C are diagrams illustrating examples of a motion contrast image in a case where a threshold is changed according to the first embodiment.
Figure 9B:
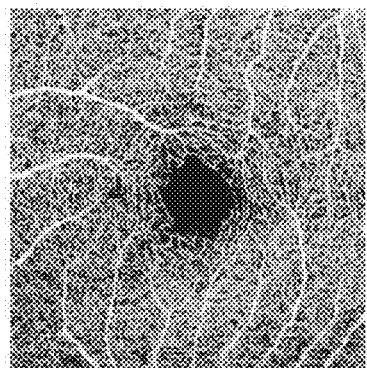
Figure 9C:
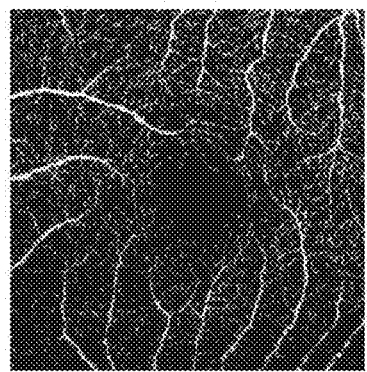

FIGS. 9A to 9C are diagrams illustrating examples of a two-dimensional motion contrast image that has been generated by projecting or integrating, in the depth direction, individual pixel values of a three-dimensional motion contrast image in the selected depth range.

Figure 8B:
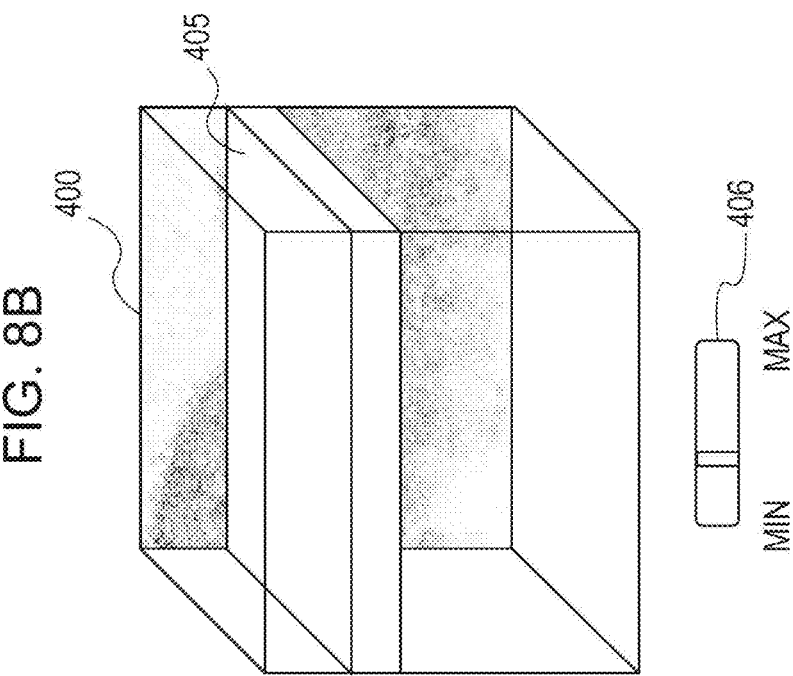
FIGS. 8A and 8B are diagrams for describing an example of a GUI according to the first embodiment.
Figure 8A:
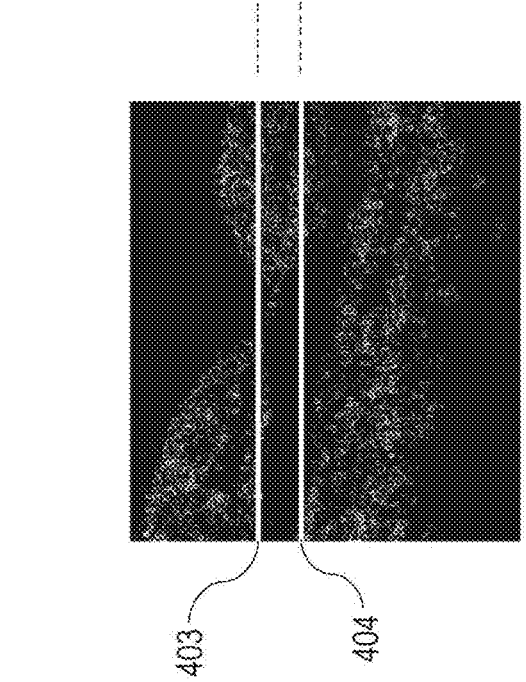

In this embodiment, the three-dimensional motion contrast image illustrated in FIG. 8B is displayed, but the embodiment is not limited thereto, and a two-dimensional motion contrast image may be displayed. For example, a two-dimensional motion contrast image may be displayed instead of a three-dimensional motion contrast image, or both the images may be simultaneously displayed.

To generate a two-dimensional motion contrast image, motion contrast values of corresponding pixels may be integrated, or a representative value such as a maximum value, a minimum value, or a median value may be extracted for projection. Here, examples of a two-dimensional motion contrast image generated through integration are illustrated in FIGS. 9A to 9C. Of course, the tester is able to change the display threshold by operating the slider 406 illustrated in FIG. 8B. FIG. 9B corresponds to a case where the threshold is an initial value that is considered to be experimentally optimum, FIG. 9A corresponds to a case where the threshold is smaller than that in FIG. 9B, and FIG. 9C corresponds to a case where the threshold is larger than that in FIG. 9B. In FIG. 9A, there is noise which makes it difficult to grasp the structure of a blood flow portion. The image illustrated in FIG. 9B may be suitable for grasping the structure of a minute blood flow portion, and the image illustrated in FIG. 9C may be suitable in the case of performing comparison with an image captured through fluorescein angiography according to the related art.

Figure 10A:
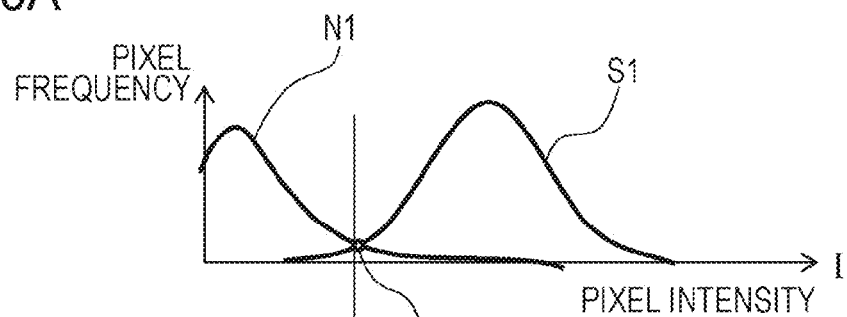
FIGS. 10A to 10C are diagrams illustrating examples of a histogram of a motion region and a non-motion region according to the first embodiment.
Figure 10B:
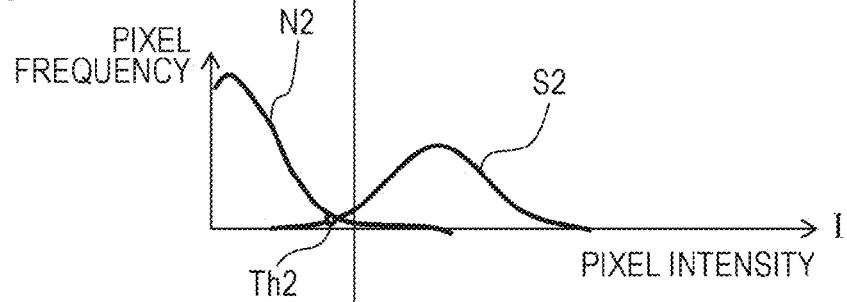
Figure 10C:
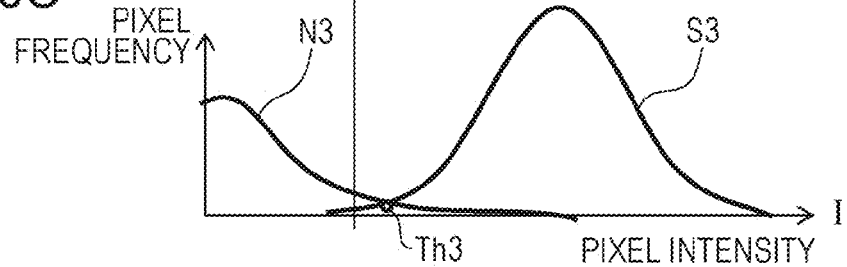

Now, a method for automatically determining a threshold will be described with reference to FIGS. 10A to 10C. FIG. 10A illustrates a histogram of a motion contrast in a certain depth range that has been selected. A noise peak N1 is observed on a low brightness side, and a signal peak S1 in a blood flow region is observed on a high brightness side. The display threshold process is programmed so that a value Th1 corresponding to an intersection point of the two peaks is an initial value of the display threshold. Of course, experimentally, it is possible to give a certain ratio or a certain amount of shift. FIGS. 10B and 10C illustrate changes in a histogram in a case where a tester changes the range in the depth direction of display. FIG. 10B illustrates a case where a range including a small number of blood flows is selected, and FIG. 10C illustrates a case where a range including a large number of blood flows is selected. As illustrated in FIGS. 10B and 10C, noise peaks N2 and N3 and signal peaks S2 and S3 in the blood flow region move, and initial values Th2 and Th3 of the display threshold suitable therefor are set. That is, the display threshold is automatically changed in conjunction with the display range of a motion contrast image. As described above, according to this embodiment, a motion region and a non-motion region can be estimated based on a histogram of a motion contrast in a certain region, and a threshold can be determined based on a histogram of the motion region and a histogram of the non-motion region.

A description has been given above of a method for determining a uniform threshold for a target region by using a histogram of a motion contrast in a display range in the depth direction as the target region, but the method is not limited thereto. For example, a local determination method may be used in which a uniform threshold is not given for the same region and a threshold is determined for a certain region in the same display region on the basis of an average value and dispersion of a motion contrast.

If the tester operates the slider 406 as described above, the value may be stored and used as a display threshold thereafter. Alternatively, a switch for returning to an initial setting may be provided.

According to the first embodiment, with use of an appropriate display threshold that is variable or a plurality of appropriate display thresholds for motion contrast data forming OCT angiography, noise generated in calculation of a motion contrast can be removed and blood flow portion information that is easily seen can be quickly provided.

If the calculation step of calculating the motion contrast includes a normalization step of normalizing the motion contrast by using an average value of pieces of pixel data corresponding to one another of the plurality of pieces of tomogram data used for the calculation, noise that occurs in calculation of the motion contrast can be effectively removed.

Further, with a display range in the depth direction being set to display the calculated motion contrast image, the display range can be easily changed and an appropriate display threshold can be set.

With the display range being limited to a certain width in the depth direction of a tomogram, an unnecessary overlapped portion of the motion contrast image can be removed, and thus an image that is easily understandable can be acquired. That is, in this embodiment, a settable display range can be limited to a certain width in the depth direction.

In this case, by further providing a detection step of detecting a layer structure of a tomogram of a subject eye from three-dimensional tomogram data, a display range in the depth direction can be selected and limited in accordance with the structure of a retina of the subject eye, and a display process suitable for an anatomic structure of the subject eye can be performed, which is more effective.

Furthermore, if a two-dimensional motion contrast image is generated by projecting and integrating a three-dimensional motion contrast in accordance with the selection of the display range, a motion contrast image that is intuitively easy to understand can be provided.

If a display unit selects or generates a tomogram at a position corresponding to a position designated in a motion contrast image from a three-dimensional motion contrast and displays the tomogram, the layer on which information is now displayed can be identified more intuitively. That is, in this embodiment, in the display step of displaying a motion contrast image, a tomogram at a position corresponding to a position designated on the motion contrast image is selected or generated from a three-dimensional motion contrast and the tomogram is displayed.

Furthermore, a threshold in a certain region can be adaptively determined based on motion contrast values of pixels around each pixel in the motion contrast image to which the threshold is applied. For example, a motion region and a non-motion region can be estimated based on a histogram of a motion contrast in a certain region, and a threshold can be adaptively determined based on histograms of the individual regions. Alternatively, a threshold can be locally determined based on an average value and dispersion of a motion contrast in a certain region. Accordingly, a motion contrast image that is more easily seen and understood can be provided.

Second Embodiment

Figure 11:
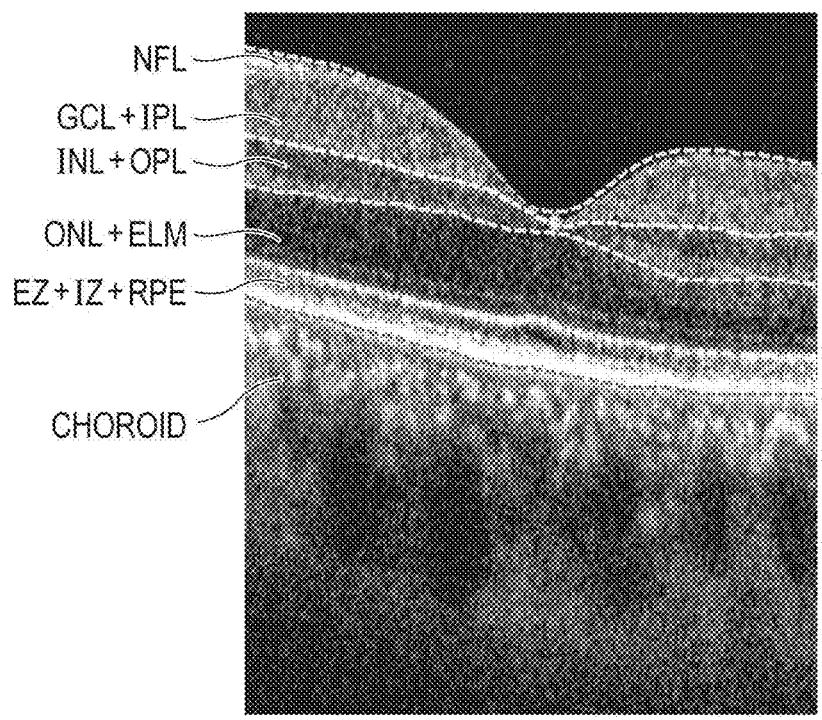
FIG. 11 is a diagram illustrating an example of a segmentation result according to a second embodiment.

In the above-described first embodiment, a description has been given of a case where a tester directly selects a display range in the depth direction. However, an ocular fundus of a subject eye which is a target of image capturing has a layer structure as illustrated in FIG. 11. In consideration of a difference in blood vessel density among retinal layers in the depth direction, a threshold for detecting a blood flow portion may be variable for each layer. Step S300 in FIG. 5, which is not used in the first embodiment, is a step of segmenting the layer structure. In this embodiment, six layers can be detected. The process in step S300 corresponds to an example of a detection step of detecting layers from tomogram data. The number of layers to be detected is not limited to six. Here, the six layers include (1) a nerve fiber layer (NFL), (2) a composite layer formed of a ganglion cell layer (GCL) and an inner plexiform layer (IPL), (3) a composite layer formed of an inner nuclear layer (INL) and an outer plexiform layer (OPL), (4) a composite layer formed of an outer nuclear layer (ONL) and an external limiting membrane (ELM), (5) a composite layer formed of an ellipsoid zone (EZ), an interdigitation zone (IZ), and a retinal pigment epithelium (RPE) layer, and (6) a choroid.

The specific process of generating three-dimensional blood flow portion information in step S102 according to this embodiment is almost the same as in the first embodiment illustrated in FIG. 5, and thus the detailed description thereof is omitted. Hereinafter, a description will be given of segmentation of a retina in step S300, which is characteristic in this embodiment.

The map generating unit 148 creates images by respectively applying a median filter and a Sobel filter to a target tomogram to be processed that has been extracted from a brightness-averaged image (hereinafter respectively referred to as a median image and a Sobel image). Subsequently, the map generating unit 148 creates profiles for each A-scan from the created median image and Sobel image. A brightness profile is created from the median image whereas a gradient profile is created from the Sobel image. Subsequently, the map generating unit 148 detects a peak in the profile created from the Sobel image. With reference to the profile of the median image corresponding to before/after the detected peak or between peaks, the borders of the individual regions of the retinal layers are extracted. The segmentation result acquired in step S300 is once held at this time. After the process has been performed similarly to that in the first embodiment, the three-dimensional blood flow portion information generation step in step S350 is performed.

The three-dimensional blood flow portion information generation step in step S350 according to the second embodiment will be described with reference to FIG. 12. In the second embodiment, a display range in the depth direction of a motion contrast image is set by selecting a layer on the basis of the result of retina segmentation in step S300. That is, a display range can be selected on the basis of detected layers.

Figure 12:
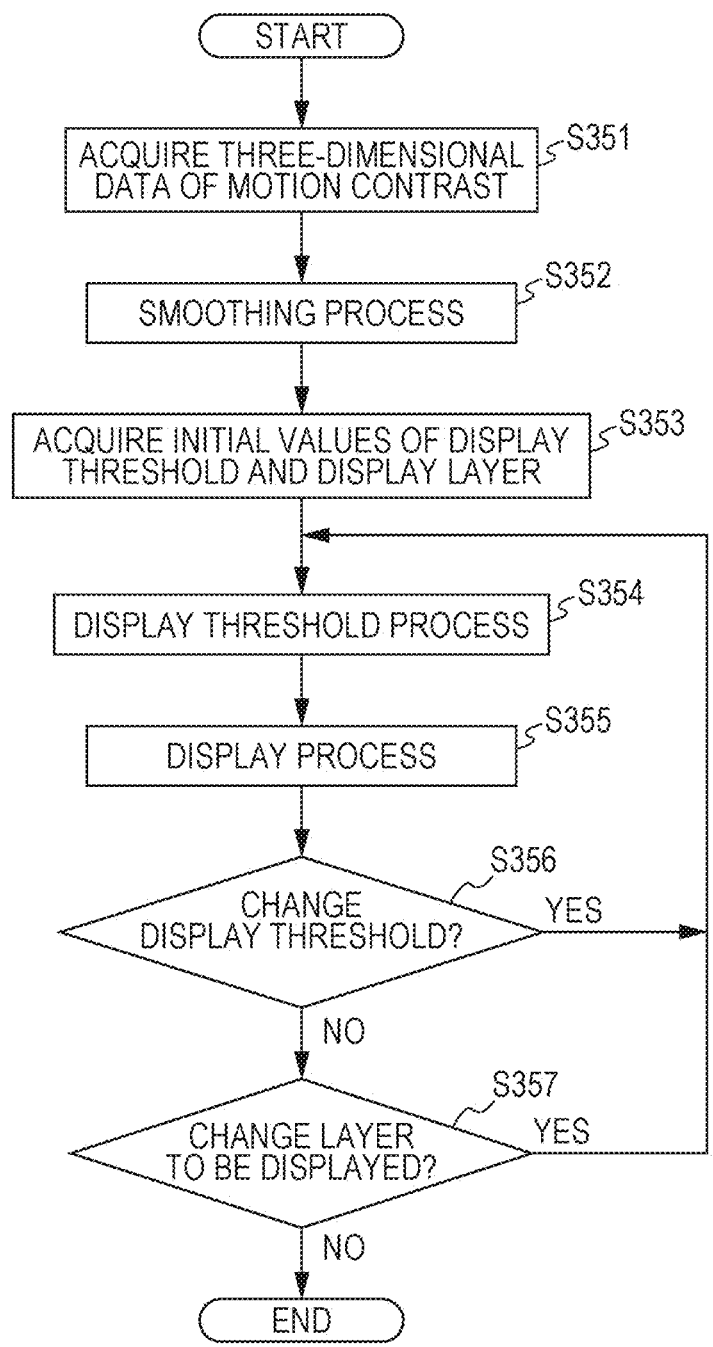
FIG. 12 is a diagram illustrating an example of a display information generation procedure according to the second embodiment.

FIG. 12 illustrates the details of step S350. This step is basically the same as in the first embodiment. That is, three-dimensional data of a motion contrast is acquired in step S351, and a smoothing process is performed on the three-dimensional motion contrast data to remove noise while keeping blood flow portion information in step S352.

In step S353, the signal processing unit 144 acquires an initial value of a display threshold for determining pixels to be displayed and an initial value of a layer to be displayed. The method for determining an initial value of a display threshold is the same as in the first embodiment. As an initial value of a display range, for example, four layers from a surface layer may be set: a nerve fiber layer (NFL); a ganglion cell layer (GCL); an inner plexiform layer (IPL); and an inner nuclear layer (INL). As the initial value, at least three layers among the four layers from the surface layer may be selected. Note that a plurality of layers selected as an initial value are consecutive layers. In the case of layers that are not able to be separated in segmentation of retinal layers, the layers may be regarded as a composite layer. Here, all the retinal layers are not set as an initial value of the display range because a main vascular plexus and a capillary plexus in a surface layer portion are to be displayed such that they are easily seen. That is, if the surface layer portion including a main vascular plexus and a capillary plexus and an RPE layer with a lot of noise that does not include blood vessels are displayed at the same time, it is difficult to identify the main vascular plexus and capillary plexus in the surface layer portion.

Figure 13:
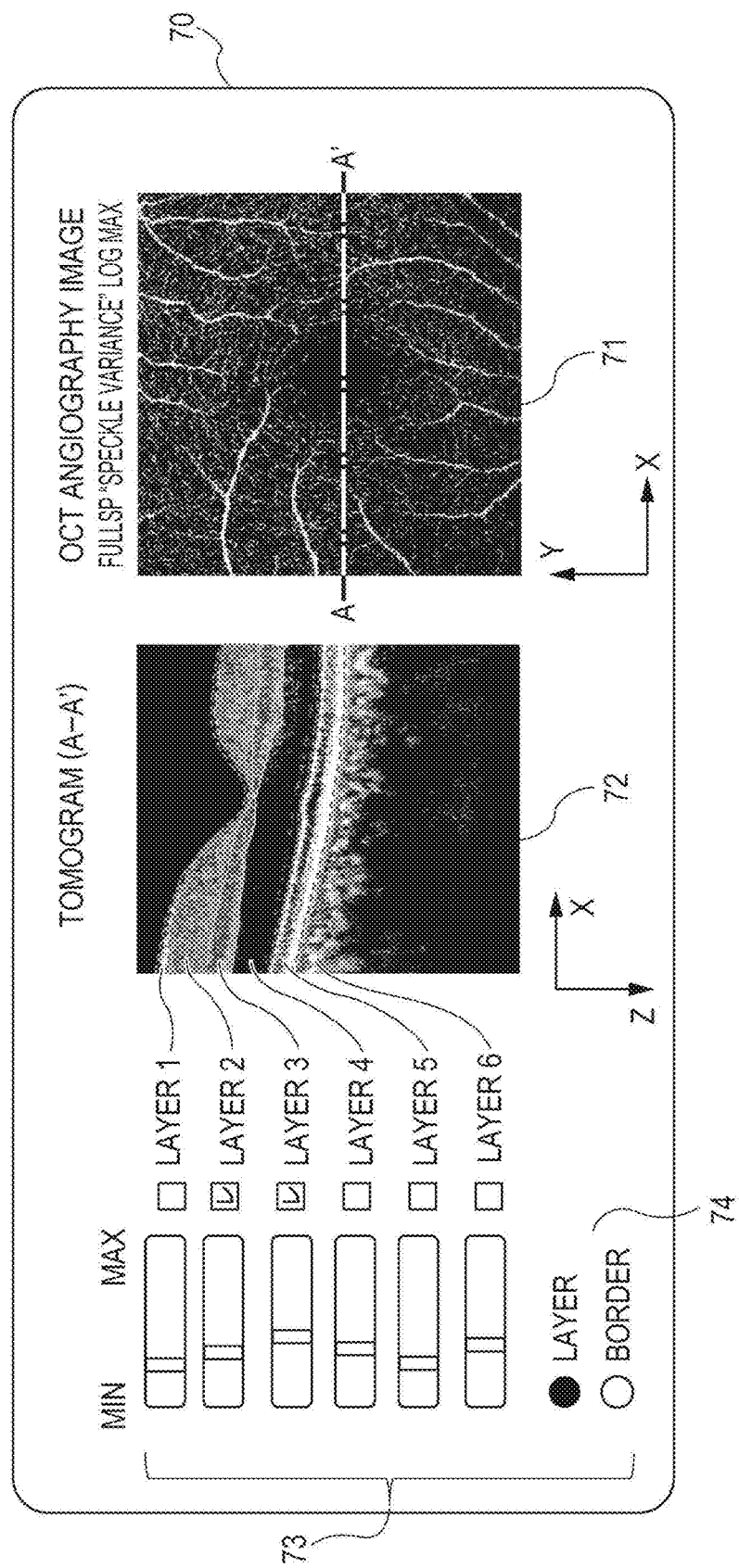
FIG. 13 is a diagram illustrating an example of a GUI according to the second embodiment.

In step S354, a display threshold process of displaying pixels exceeding the same initial value is performed on the three-dimensional data that has been subjected to a smoothing process by using the initial value. In step S355, a step of displaying a motion contrast image illustrated in FIG. 13 that has been subjected to the display threshold process is performed. For example, as illustrated in FIG. 13, a two-dimensional motion contrast image 71 is displayed on the display unit 146 by the display control unit 149. Beside the two-dimensional motion contrast image 71, a tomogram 72 corresponding to the position indicated by a marker A-A' shown in the two-dimensional motion contrast image 71 and a GUI 73 are displayed.

The GUI 73 is provided beside the tomogram 72. The configuration thereof includes, from the right, the names of retinal layers used for displaying a two-dimensional motion contrast image, check boxes for selecting the retinal layers, and sliders each for adjusting the threshold for determining pixels to be displayed for the selected layer. When the tester drags any one of the sliders with a mouse, a display threshold is changed in step S356 in FIG. 12, the process returns to step S354, and the two-dimensional motion contrast image to be displayed is updated. That is, as indicated by the GUI 73, a threshold is set for each detected layer in this embodiment.

When the tester changes the check in a check box to change the layer to be selected (corresponding to change of a display range in the depth direction in the first embodiment), the layer to be displayed in the motion contrast image is changed in step S357, the process returns to step S354, and the two-dimensional motion contrast image is updated.

In this case, if the number of layers to be selected is limited to five and if an upper retinal layer is selected (for example, any of a nerve fiber layer (NFL), a ganglion cell layer (GCL), an inner plexiform layer (IPL), an inner nuclear layer (INL), an outer plexiform layer (OPL), an outer nuclear layer (ONL), and an external limiting membrane (ELM)), one of at least an ellipsoid zone (EZ), an interdigitation zone (IZ), an RPE layer, and a choroid is unselectable. Alternatively, if a lower retinal layer is selected (for example, any of an inner nuclear layer (INL), an outer plexiform layer (OPL), an outer nuclear layer (ONL), an external limiting membrane (ELM), an ellipsoid zone (EZ), an interdigitation zone (IZ), an RPE layer, and a choroid), one of at least a nerve fiber layer (NFL), a ganglion cell layer (GCL), an inner plexiform layer (IPL), an inner nuclear layer (INL), an outer plexiform layer (OPL), an outer nuclear layer (ONL), and an external limiting membrane (ELM) may be unselectable. Such control is also effective to maintain the diagnostic value of the motion contrast image to be displayed. As described above, in this embodiment, a layer is selectable based on a detected layer in the setting of a display range, and the number of selectable layers can be limited.

A tomogram may be displayed such that borders of individual layers as a result of segmentation are superposed on the tomogram, and marking may be performed on the tomogram so that a selected layer is easily recognized. A radio button 74 representing "Layer" and "Border" at the bottom of the GUI 73 is used to select a method for generating a two-dimensional motion contrast image. When "Layer" is selected, a two-dimensional motion contrast image is generated based on information representing individual pixel values of a three-dimensional motion contrast image of the entire area of the selected layers. When "Border" is selected, control is performed so that the selectable check boxes are limited to two adjacent check boxes, and a two-dimensional motion contrast image is generated based on information representing individual pixel values of a three-dimensional motion contrast image at a certain depth sandwiching the border of the two selected layers.

The first embodiment and the second embodiment may be combined. For example, the slider 406 illustrated in FIG. 8B may be displayed on the screen illustrated in FIG. 13.

According to this embodiment, a display range of a motion contrast image can be easily set by using a result of segmentation.

Third Embodiment

In the second embodiment, a description has been given of an example of using, as portion structure information, a result of segmentation acquired based on brightness information in order to clarify three-dimensional blood flow portion information. In contrast, in a third embodiment, a description will be given of an example of acquiring portion structure information using polarization information of optical coherence tomography as portion structure information.

Figure 14:
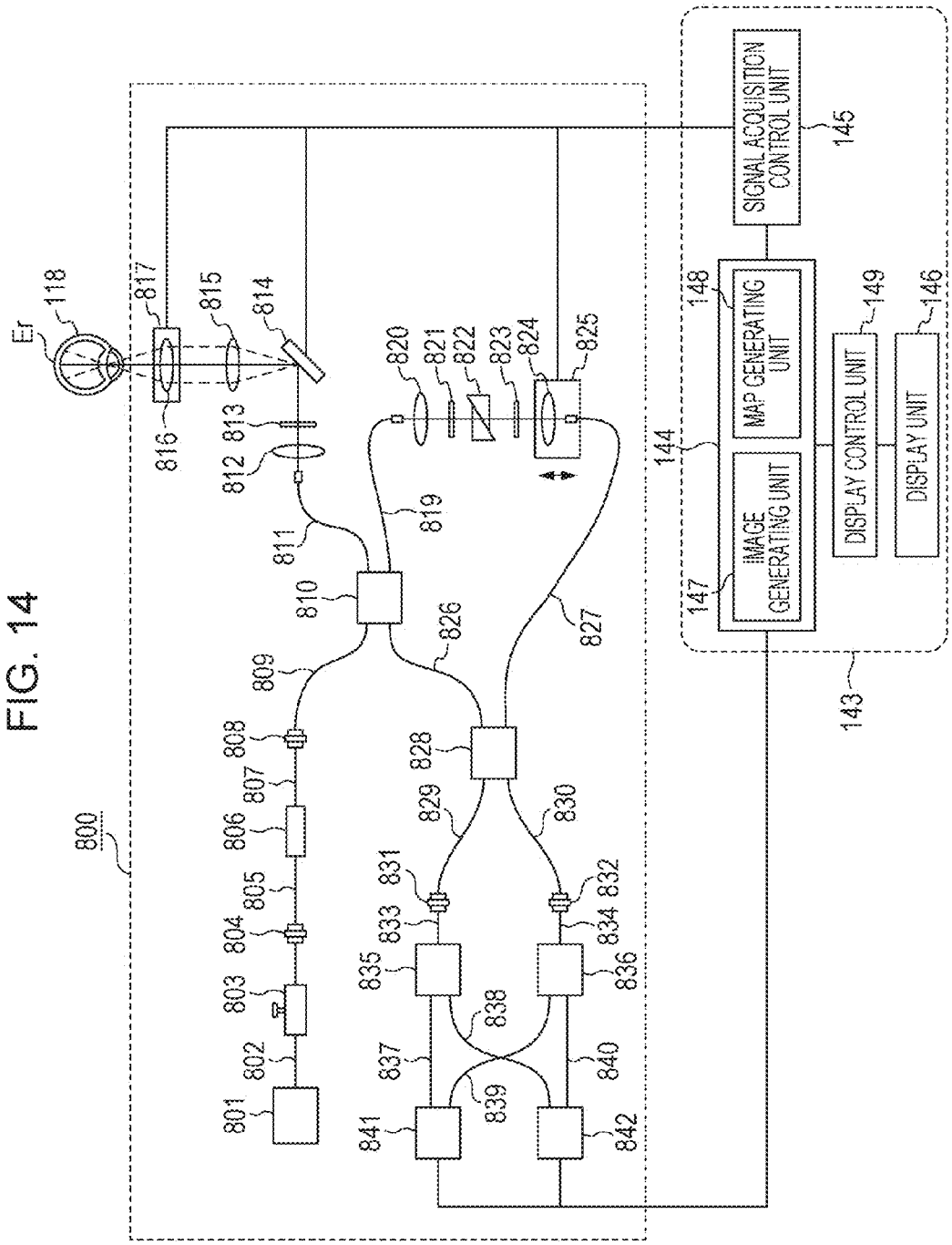
FIG. 14 is a diagram illustrating an overview of an example of the overall configuration of an apparatus according to a third embodiment.

FIG. 14 is a diagram illustrating an example configuration of an image forming apparatus using optical coherence tomography (OCT) according to the third embodiment. The image forming apparatus includes an OCT signal acquiring unit 800 that acquires an OCT signal and the control unit 143. The control unit 143 includes the signal processing unit 144, the signal acquisition control unit 145, the display control unit 149 and the display unit 146. The signal processing unit 144 includes the image generating unit 147 and the map generating unit 148.

The configuration of the OCT signal acquiring unit 800 will be described. In this embodiment, a description will be given of a polarization OCT apparatus based on SS-OCT. An embodiment of the present invention is also applicable to a polarization OCT apparatus based on SD-OCT.
Configuration of Polarization OCT Apparatus 800

The configuration of the polarization OCT apparatus 800 will be described below.

A light source 801 is a swept source (SS) type light source, and emits light while performing wavelength sweeping with a center sweep wavelength of 1050 nm and a sweep width of 100 nm.

The light emitted from the light source 801 is led to a beam splitter 810 via a single mode fiber (SM fiber) 802, a polarization controller 803, a connector 804, an SM fiber 805, a polarizer 806, a polarization maintaining (PM) fiber (PM fiber) 807, a connector 808, and a PM fiber 809, and is split into measurement light (also referred to as OCT measurement light) and reference light (also referred to as reference light corresponding to the OCT measurement light). The split ratio of the beam splitter 810 is 90 (reference light):10 (measurement light). The polarization controller 803 is programmed to change the polarization state of the light emitted from the light source 801 to a desired polarization state. The polarizer 806 is an optical device having a characteristic of causing only a specific linear polarization component to pass therethrough. Normally, the light emitted from the light source 801 has a high degree of polarization and a light component having a specific polarization direction is dominant. However, the light contains a light component not having a specific polarization direction, called a random polarization component. The random polarization component deteriorates the quality of a polarization OCT image and is thus removed by the polarizer 806. Only specific linearly polarized light can pass through the polarizer 806. Thus, the polarization state is adjusted by the polarization controller 803 so that a desired amount of light will enter the subject eye 118.

The split measurement light is emitted via a PM fiber 811 and is formed into parallel light by a collimator 812. The measurement light that has become parallel light passes through a quarter-wave plate 813 and then enters the subject eye 118 via a galvano scanner 814 that performs scan at the ocular fundus Er of the subject eye 118, a scan lens 815, and a focus lens 816. Although the galvano scanner 814 is illustrated as a single mirror, it actually includes two galvano scanners to raster scan the ocular fundus Er of the subject eye 118. The focus lens 816 is fixed onto a stage 817 and is controlled to perform focus adjustment by moving in the optical-axis direction. The galvano scanner 814 and the stage 817 are controlled by the signal acquisition control unit 145, and scanning can be performed with measurement light in a desired range of the ocular fundus Er of the subject eye 118 (also referred to as a tomogram acquisition range, a tomogram acquisition position, or a measurement light irradiation position). The quarter-wave plate 813 is an optical device having a characteristic of retarding, by a quarter wavelength, the phase between the optical axis of the quarter-wave plate and the axis orthogonal to the optical axis. In this embodiment, the optical axis of the quarter-wave plate 813 is rotated 45 degrees, by using a light axis as a rotation axis, with respect to the direction of linear polarization of the measurement light emitted from the PM fiber 811, so that circularly polarized light enters the subject eye 118. Although a detailed description is not given in this embodiment, a tracking function may be provided in which a movement of the ocular fundus Er is detected and the mirror of the galvano scanner 814 is caused to track the movement of the ocular fundus Er to perform scan. Tracking may be performed by using a typical technique, and may be performed in real time or in post-processing. For example, there is a method of using a scanning laser ophthalmoscope (SLO). In this method, a two-dimensional image in a plane vertical to an optical axis of the ocular fundus Er is chronologically acquired by using an SLO, and a characteristic portion such as a branch of a blood vessel is extracted from the image. A movement at the characteristic portion in the acquired two-dimensional image is calculated as an amount of movement of the ocular fundus Er, the calculated amount of movement is fed back to the galvano scanner 814, and thereby real-time tracking can be performed.

The measurement light is caused to enter the subject eye 118 by the focus lens 816 on the stage 817 and is focused on the ocular fundus Er. The measurement light with which the ocular fundus Er has been irradiated is reflected or scattered at each retinal layer and returns along the above-described optical path to the beam splitter 810. The returned measurement light that has entered the beam splitter 810 enters a beam splitter 828 via a PM fiber 826.

On the other hand, the reference light generated through split at the beam splitter 810 is emitted via a PM fiber 819 and is formed into parallel light by a collimator 820. The reference light enters a PM fiber 827 via a half-wave plate 821, a dispersion compensation glass 822, an ND filter 823, and a collimator 824. One end of the collimator 824 and one end of the PM fiber 827 are fixed onto a coherence gate stage 825, which is controlled by the signal acquisition control unit 145 so as to be driven in the optical-axis direction in accordance with a difference in ocular axis length of a subject. The half-wave plate 821 is an optical device having a characteristic of retarding, by a half wavelength, the phase between the optical axis of the half-wave plate and the axis orthogonal to the optical axis. In this embodiment, adjustment is performed so that the linearly polarized light of the reference light emitted from the PM fiber 819 is in a polarization state in which the long axis is inclined 45 degrees in the PM fiber 827. In this embodiment, the optical path length of the reference light is changed, but it is sufficient that a difference in optical path length between the optical path of the measurement light and the optical path of the reference light can be changed.

The reference light that has passed through the PM fiber 827 enters the beam splitter 828. At the beam splitter 828, the returned measurement light and the reference light are combined into coherent light, which is then divided into two coherent light beams. The two coherent light beams acquired through division have phases inverted to each other (hereinafter referred to as a positive component and a negative component). The positive component of the coherent light beam enters a polarizing beam splitter 835 via a PM fiber 829, a connector 831, and a PM fiber 833. On the other hand, the negative component of the coherent light beam enters a polarizing beam splitter 836 via a PM fiber 830, a connector 832, and a PM fiber 834.

At the polarizing beam splitters 835 and 836, coherent light is divided, in accordance with two polarization axes orthogonal to each other, into two light beams corresponding to a vertical polarization component (V polarization component) and a horizontal polarization component (H polarization component). Positive coherent light that has entered the polarizing beam splitter 835 is divided by the polarizing beam splitter 835 into two coherent light beams corresponding to a positive V polarization component and a positive H polarization component. The positive V polarization component acquired through division enters a detector 841 via a PM fiber 837, and the positive H polarization component enters a detector 842 via a PM fiber 838. On the other hand, negative coherent light that has entered the polarizing beam splitter 836 is divided by the polarizing beam splitter 836 into a negative V polarization component and a negative H polarization component. The negative V polarization component enters the detector 841 via a PM fiber 839, and the negative H polarization component enters the detector 842 via a PM fiber 840.

Both the detectors 841 and 842 serve as a differential detector. When two coherent signals having phases inverted by 180 degrees to each other are input thereto, the detectors 841 and 842 remove a direct current component and outputs only a coherent component.

The V polarization component of a coherent signal detected by the detector 841 and the H polarization component of a coherent signal detected by the detector 842 are output as electric signals corresponding to the intensity of light, and are input to the signal processing unit 144, which is an example of a tomogram generating unit.

Control Unit 143

The control unit 143 for controlling the overall apparatus will be described.

The control unit 143 includes the signal processing unit 144, the signal acquisition control unit 145, the display unit 146, and the display control unit 149. The signal processing unit 144 includes the image generating unit 147 and the map generating unit 148. The image generating unit 147 has a function of generating a brightness image and a polarization characteristic image from an electric signal transmitted to the signal processing unit 144. The map generating unit 148 has a function of detecting a nerve fascicle and a retinal pigment epithelium.

The signal acquisition control unit 145 controls the individual units in the manner described above. The signal processing unit 144 generates an image, analyzes the generated image, and generates visualized information representing the analysis result on the basis of the signals output from the detectors 841 and 842.

The display unit 146 and the display control unit 149 are almost the same as those according to the first embodiment, and thus the detailed description thereof is omitted.

Image Processing

Next, image generation performed by the signal processing unit 144 will be described. The signal processing unit 144 performs, in the image generating unit 147, a typical reconstruction process on coherent signals output from the detectors 841 and 842. With this process, the signal processing unit 144 generates two tomograms based on individual polarization components, that is, a tomogram corresponding to the H polarization component and a tomogram corresponding to the V polarization component.

First, the image generating unit 147 performs fixed pattern noise removal on a coherent signal. The fixed pattern noise removal is performed by extracting fixed pattern noise by averaging a plurality of A-scan signals that have been detected and by subtracting the fixed pattern noise from the input coherent signal. Subsequently, the image generating unit 147 performs a desired window function process to optimize depth resolution and dynamic range that have a tradeoff relationship in a case where Fourier transform is performed in a limited section. Subsequently, the image generating unit 147 performs an FFT process to generate a tomography signal.

With the above-described process being performed on the coherent signal having the two polarization components, two tomograms are generated. On the basis of the tomography signals and tomograms, a brightness image and a polarization characteristic image are generated. The polarization characteristic image is an image representing a polarization characteristic of a subject eye and includes, for example, an image based on retardation information, an image based on orientation information, and an image based on birefringence information.

Generation of Brightness Image

The image generating unit 147 generates a brightness image from the above-described two tomography signals. The brightness image is basically the same as a tomogram of OCT according to the related art (as in step S250 according to the first embodiment), and a pixel value r thereof is calculated by using Equation 1 from a tomography signal $A_H$ of the H polarization component and a tomography signal $A_V$ of the V polarization component acquired from the detectors 841 and 842.

$$r = \sqrt{A_H^2 + A_V^2} \quad \text{Equation 1}$$

Also, raster scan is performed by using the galvano scanner 814 to arrange B-scan images of the ocular fundus Er of the subject eye 118 in the sub-scan direction, thereby generating three-dimensional data of a brightness image.

With the process described in the first embodiment being applied, an image of the ocular fundus Er is captured by using a scan pattern for OCT angiography, and OCT angiography is acquired from the brightness image calculated in the above-described manner.

The retinal pigment epithelium (RPE) has a nature of cancelling polarization, and thus the signal processing unit 144 detects the RPE on the basis of the nature.

RPE Segmentation
Generation of DOPU Image

The image generating unit 147 calculates, for each pixel, a Stokes vector S by using Equation 2 from the acquired tomography signals $A_H$ and $A_V$ and the phase difference $\Delta\Phi$ therebetween.

$$S = \begin{pmatrix} I \\ Q \\ U \\ V \end{pmatrix} = \begin{pmatrix} A_H^2 + A_V^2 \\ A_H^2 - A_V^2 \\ 2A_H A_V \cos\Delta\phi \\ 2A_H A_V \sin\Delta\phi \end{pmatrix} \quad \text{Equation 2}$$

Note that $\Delta\Phi$ is calculated as $\Delta\Phi = \Phi_V - \Phi_H$ from the phases $\Phi_H$ and $\Phi_V$ of each signal acquired in the case of calculating two tomograms.

Subsequently, the image generating unit 147 sets windows for individual B-scan images, each window having a size of 70 μm in the main scan direction of measurement light and 18 μm in the depth direction, individual elements of the Stokes vector calculated for each pixel by using Equation 2 are averaged in each window, and a degree of polarization uniformity (DOPU) in the window is calculated by using Equation 3.

$$\text{DOPU} = \sqrt{Q_m^2 + U_m^2 + V_m^2} \quad \text{Equation 3}$$

Note that $Q_m$, $U_m$, and $V_m$ are average values of elements Q, U, and V of the Stokes vector in each window. This process is performed on all the windows in the B-scan image and thereby a DOPU image (also referred to as a tomogram representing a degree of polarization uniformity) is generated.

DOPU is a value representing a degree of polarization uniformity, becomes approximate to 1 at a position where polarization is kept, and becomes a value smaller than 1 at a position where polarization is not kept. In the structure in a retina, RPE has a nature of canceling a polarization state, and thus the portion corresponding to the RPE in a DOPU image has a small value relative to the other region. The DOPU image is an image representing a layer in which polarization is to be cancelled, such as the RPE. Thus, even if the RPE is deformed by a disease, an image of the RPE can be generated more reliably than an image of a change in brightness.

Segmentation information about the RPE is acquired from the DOPU image.

With this process, it is determined whether each position corresponds to the RPE by using a coherent signal (three-dimensional data) that has been captured.

Processing Operation

Next, a procedure of a specific process of the image formation method according to this embodiment will be described. A basic process flow according to this embodiment is the same as the process flow according to the first embodiment, and thus the description of the outline is omitted. However, the details of steps S250, S300, and S320 are different, and thus a detailed description will be given below of steps S250A, S300A, and S320A according to this embodiment corresponding to the respective steps.

In step S250A, the signal processing unit 144 generates a tomogram $A_H$ and a tomogram $A_V$ and also generates a brightness image. Further, the signal processing unit 144 generates a DOPU image.

In step S300A, the map generating unit 148 performs RPE segmentation by using the brightness image and the DOPU image.

In step S320A, the signal processing unit 144 corrects OCT angiography information (here, motion contrast) by using the portion information (retina segmentation information) acquired in step S300A. Here, a noise threshold (first threshold) of a motion contrast in the RPE is increased by using DOPU information (information which is RPE) of pixels acquired from the retina segmentation information. For example, a threshold related to the RPE is made larger than a threshold related to an upper region of the RPE. Alternatively, a motion contrast is decreased so that a blood flow portion is not displayed. Accordingly, the threshold process performed in step S320A can be performed more accurately. Alternatively, a threshold for a region deeper than the RPE may be made larger than a threshold for the other region, so as to reduce noise at a deep position.

With use of the above-described polarization OCT apparatus, RPE segmentation can be acquired, noise can be reduced more accurately from three-dimensional data of a motion contrast, and clear three-dimensional blood flow portion information can be acquired. Furthermore, display of an unclear blood flow portion can be prevented.

The display threshold in step S354 may be controlled as in the case of the above-described noise threshold. Noise at a deep position may be reduced by, for example, setting the display threshold for a portion deeper than the RPE to be larger than the threshold for the other regions. Alternatively, the display threshold related to the RPE may be set to be larger than the display threshold for the region above the RPE.

Fourth Embodiment

In the third embodiment, a description has been given of an example of acquiring structure information about an RPE using polarization information about an optical coherence tomography as portion structure information. In a fourth embodiment, a description will be given of an example of acquiring structure information about a retinal nerve fiber layer (RNFL).

An example configuration of an image forming apparatus according to this embodiment is the same as that in the third embodiment illustrated in FIG. 14, and thus the description thereof is omitted here.

An example of a layer having birefringence is a retinal nerve fiber layer (RNFL). The signal processing unit 144 according to this embodiment detects an RNFL on the basis of its nature.

Generation of Retardation Image

The image generating unit 147 generates a retardation image from tomograms having polarization components that are orthogonal to each other.

A value δ of each pixel of the retardation image is a value representing a phase difference between a vertical polarization component and a horizontal polarization component at the position of the pixel constituting a tomogram, and is calculated by using Equation 4 from tomography signals $A_H$ and $A_V$.

$$\delta = \arctan\left[\frac{A_V}{A_H}\right] \qquad \text{Equation 4}$$

With the retardation image being generated, a layer having birefringence, such as a retinal nerve fiber layer (RNFL), is grasped.

The signal processing unit 144 detects a retinal nerve fiber layer (RNFL) from the retardation image acquired for a plurality of B-scan images.

Generation of Retardation Map

The signal processing unit 144 generates a retardation map from the retardation images acquired for a plurality of B-scan images.

First, the signal processing unit 144 detects a retinal pigment epithelium (RPE) in each B-scan image. Since the RPE has a nature of cancelling polarization, distribution of retardation in each A-scan is examined along the depth direction in the range that does not include the inner limiting membrane (ILM) to the RPE, and the maximum value is regarded as a representative value of retardation in the A-scan.

The map generating unit 148 performs the above-described process on all the retardation images and thereby generates a retardation map.

RNFL Segmentation

Generation of Birefringence Map

The image generating unit 147 performs linear approximation on the values of retardation S in the range from the ILM to the RNFL in each A-scan image of the generated retardation image, and determines the slope thereof as birefringence at a position on the retina of the A-scan image. This process is performed on all the retardation images that have been acquired, thereby generating a map representing birefringence. Subsequently, the map generating unit 148 performs RNFL segmentation by using a birefringence value.

Processing Operation

Next, a procedure of a specific process of the image formation method according to this embodiment will be described. A basic process flow according to this embodiment is the same as the process flow according to the third embodiment, and thus the description of the outline is omitted. However, the details of steps S250A, S300A, and S320A are different, and thus a detailed description will be given below of steps S250B, S300B, and S320B according to this embodiment corresponding to the respective steps.

In step S250B, the signal processing unit 144 generates a tomogram $A_H$ and a tomogram $A_V$ and also generates a brightness image. Further, the signal processing unit 144 generates a retardation image.

In step S300B, the map generating unit 148 performs generation of a retardation map and RNFL segmentation by using the brightness image and the retardation image.

In step S320B, the signal processing unit 144 corrects OCT angiography information (here, motion contrast) by using the portion information (retina segmentation information) acquired in step S300B. Here, a noise threshold (first threshold) of a motion contrast in the RNFL is increased by using pixel retardation information (information which is RNFL) acquired from the retina segmentation information. Alternatively, a motion contrast is decreased so that a blood flow portion is not displayed. Accordingly, the threshold process performed in step S320B can be performed more accurately.

With use of the above-described polarization OCT apparatus, RNFL segmentation can be acquired, noise can be reduced more accurately from three-dimensional data of a motion contrast, and clear three-dimensional blood flow portion information can be acquired.

The display threshold in step S354 may be controlled as in the case of the above-described noise threshold.

A description has been given of a method for acquiring clearer three-dimensional blood flow portion information by performing RPE or RNFL segmentation using information about polarization OCT. This embodiment is not limited to RPE or RNFL and may be applied to other portions.

Furthermore, a blood vessel can be specified by using a polarization characteristic of a blood vessel wall and the reliability of a result of combination with motion contrast information can be enhanced.

Other Embodiments

Embodiments of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiments and/or that includes one or more circuits (e.g., application specific integrated circuit (ASIC)) for performing the functions of one or more of the above-described embodiments, and by a method performed by the computer of the system or apparatus by, for example, reading out and executing the computer executable instructions from the storage medium to perform the functions of one or more of the above-described embodiments and/or controlling the one or more circuits to perform the functions of one or more of the above-described embodiments. The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-094339, filed May 1, 2015, which is hereby incorporated by reference herein in its entirety.

What is claimed is:

1. An image generation method comprising:
   an acquisition step of acquiring a plurality of pieces of tomogram data of a subject, the plurality of pieces of tomogram data representing cross-sections at a substantially identical portion of the subject;
   a calculation step of calculating a motion contrast value by using pieces of pixel data corresponding to one another among the plurality of pieces of tomogram data that have been acquired;
   a comparison step of comparing the motion contrast value with a threshold for generating a motion contrast image of the subject;
   a generation step of generating the motion contrast image based on a result of the comparing; and
   a change step of changing the threshold,
   wherein at least one processor in communication with at least one memory configured to perform the acquisition step, calculation step, comparison step, generation step and changing step.

2. The image generation method according to claim 1, wherein the calculation step includes a normalization step of normalizing the motion contrast value by using an average value of the pieces of pixel data corresponding to one another among the plurality of pieces of tomogram data used in the calculation step.

3. The image generation method according to claim 1, further comprising:
   a set step of setting a display range in a depth direction of the motion contrast image; and
   a display step of displaying the motion contrast image in accordance with the display range that has been set,
   wherein the motion contrast image to be displayed is updated in accordance with a change in the display range.

4. The image generation method according to claim 3, wherein the set step limits a settable display range to a certain width in the depth direction.

5. The image generation method according to claim 4, wherein the generation step and the display step are repeatedly performed in accordance with a change in the threshold.

6. The image generation method according to claim 3, further comprising:
   a detection step of detecting a layer from the pieces of tomogram data,
   wherein the set step selects a display range in accordance with the layer that has been detected.

7. The image generation method according to claim 6, wherein the set step selects a layer in accordance with the layer that has been detected and limits a total number of selectable layers.

8. The image generation method according to claim 7, wherein
   the subject is an ocular fundus,
   the set step selects an upper retinal layer of the ocular fundus, and
   if any of a nerve fiber layer (NFL), a ganglion cell layer (GCL), an inner plexiform layer (IPL), an inner nuclear layer (INL), an outer plexiform layer (OPL), an outer nuclear layer (ONL), and an external limiting membrane (ELM) is selected, one of at least an ellipsoid zone (EZ), an interdigitation zone (IZ), a retinal pigment epithelium (RPE) layer, and a choroid is unselectable.

9. The image generation method according to claim 8, wherein the generation step and the display step are repeatedly performed in accordance with a change in the threshold.

10. The image generation method according to claim 7, wherein
    the subject is an ocular fundus,
    the set step selects a lower retinal layer, and
    if any of an inner nuclear layer (INL), an outer plexiform layer (OPL), an outer nuclear layer (ONL), an external limiting membrane (ELM), an ellipsoid zone (EZ), an interdigitation zone (IZ), a retinal pigment epithelium (RPE) layer, and a choroid is selected, one of at least a nerve fiber layer (NFL), a ganglion cell layer (GCL), an inner plexiform layer (IPL), an inner nuclear layer (INL), an outer plexiform layer (OPL), an outer nuclear layer (ONL), and an external limiting membrane (ELM) is unselectable.

11. The image generation method according to claim 7, wherein the generation step and the display step are repeatedly performed in accordance with a change in the threshold.

12. The image generation method according to claim 6, wherein the generation step and the display step are repeatedly performed in accordance with a change in the threshold.

13. The image generation method according to claim 6, wherein the threshold is set for each layer that has been detected.

14. The image generation method according to claim 3, wherein
    each of the plurality of pieces of tomogram data is three-dimensional tomogram data,
    the calculation step includes calculating a three-dimensional motion contrast value,
    the generation step includes generating a two-dimensional motion contrast image by projecting or integrating the three-dimensional motion contrast value in the depth direction in the display range, and
    the display step includes displaying the two-dimensional motion contrast image.

15. The image generation method according to claim 14, wherein the display step includes selecting or generating, based on the three-dimensional motion contrast value, a tomogram at a position corresponding to a position designated on the motion contrast image, and displaying the tomogram.

16. The image generation method according to claim 3, wherein the generation step and the display step are repeatedly performed in accordance with a change in the threshold.

17. The image generation method according to claim 1, wherein the threshold is determined in accordance with a motion contrast value of a surrounding pixel of an image corresponding to the motion contrast value compared with the threshold.

18. The image generation method according to claim 1, wherein a motion region and a non-motion region are estimated from a histogram of a motion contrast value in a certain region, and the threshold is determined based on a histogram of the motion region and a histogram of the non-motion region.

19. A non-transitory computer-readable storage medium that stores a program which causes a computer to execute the image generation method according to claim 1.

20. The image generation method according to claim 1, wherein a brightness, in the motion contrast image, corresponding to the motion contrast value that is lower than the threshold is set to a predetermined value.

21. The image generation method according to claim 20, wherein the predetermined value is zero.

22. The image generation method according to claim 1, further comprising:
    a display step of displaying the motion contrast image,
    wherein the generation step and the display step are repeatedly performed in accordance with a change in the threshold.

23. The image generation method according to claim 1, wherein the subject is a fundus of an eye.

24. The image generation method according to claim 1, wherein a brightness, in the motion contrast image, corresponding to the motion contrast value that is higher than the threshold increases in accordance with an increase of the motion contrast value.

25. An image generation apparatus comprising:
    an acquiring unit configured to acquire a plurality of pieces of tomogram data of a subject, the plurality of pieces of tomogram data representing cross-sections at a substantially identical portion of the subject;
    a calculating unit configured to calculate a motion contrast value by using pieces of pixel data corresponding to one another among the plurality of pieces of tomogram data that have been acquired;
    a comparing unit configured to compare the motion contrast value with a threshold for generating a motion contrast image of the subject;
    a generating unit configured to generate the motion contrast image based on a result of the comparing; and
    a changing unit configured to change the threshold.

26. The image generation apparatus according to claim 25, wherein a brightness, in the motion contrast image, corresponding to the motion contrast value that is lower than the threshold is set to a predetermined value.

27. The image generation apparatus according to claim 26, wherein the predetermined value is zero.

28. The image generation apparatus according to claim 25, further comprising:
    a displaying unit configured to display the motion contrast image,
    wherein the generation by the generation unit and the displaying by the display unit are repeatedly performed in accordance with a change in the threshold.

29. The image generation apparatus according to claim 25, wherein the subject is a fundus of an eye.

30. The image generation apparatus according to claim 29, wherein the changing unit independently changes the threshold for respective layers of the fundus.

31. The image generation apparatus according to claim 25, wherein a brightness, in the motion contrast image, corresponding to the motion contrast value that is higher than the threshold increases in accordance with an increase of the motion contrast value.

* * * * *